US009751922B2

(12) United States Patent
Goshima et al.

(10) Patent No.: US 9,751,922 B2
(45) Date of Patent: Sep. 5, 2017

(54) PROTEIN TAG, TAGGED PROTEIN, AND PROTEIN PURIFICATION METHOD

(71) Applicant: NATIONAL INSTITUTE OF ADVANCED INDUSTRIAL SCIENCE AND TECHNOLOGY, Tokyo (JP)

(72) Inventors: Naoki Goshima, Tokyo (JP); Eriko Fukuda, Tokyo (JP); Masatoshi Mori, Tokyo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 216 days.

(21) Appl. No.: 14/390,957

(22) PCT Filed: Nov. 21, 2012

(86) PCT No.: PCT/JP2012/080133
§ 371 (c)(1),
(2) Date: Oct. 6, 2014

(87) PCT Pub. No.: WO2013/150680
PCT Pub. Date: Oct. 10, 2013

(65) Prior Publication Data
US 2015/0166619 A1 Jun. 18, 2015

(30) Foreign Application Priority Data
Apr. 6, 2012 (JP) ................. 2012-087214

(51) Int. Cl.
C12P 21/04 (2006.01)
C07K 14/47 (2006.01)
C12P 21/02 (2006.01)
C12N 15/67 (2006.01)

(52) U.S. Cl.
CPC .......... *C07K 14/4702* (2013.01); *C12N 15/67* (2013.01); *C12P 21/02* (2013.01); *C07K 2319/50* (2013.01)

(58) Field of Classification Search
None
See application file for complete search history.

(56) References Cited

U.S. PATENT DOCUMENTS

| 2004/0086521 | A1 | 5/2004 | Kropshofer et al. |
| 2004/0142388 | A1 | 7/2004 | Lamping et al. |
| 2004/0152138 | A1 | 8/2004 | Lamping et al. |
| 2006/0263855 | A1 | 11/2006 | Wood et al. |

FOREIGN PATENT DOCUMENTS

| JP | 6-277088 A | 10/1994 |
| JP | 2003-292500 A | 10/2003 |
| JP | 2004-531250 A | 10/2004 |
| JP | 2004-532633 A | 10/2004 |
| JP | 2006-145470 A | 6/2006 |
| JP | 2004-123749 A | 4/2007 |
| JP | 2009-537812 A | 10/2009 |
| WO | WO 00/06763 A1 | 2/2000 |
| WO | 2007/132291 A2 | 11/2007 |

OTHER PUBLICATIONS

Blank et al., Blood, 1997, 89: 3925-3935.*
Toki et al., Oncogene, 1997, 14: 1901-1910.*
Olsen et al., Molecular & Cellular Proteomics, 2004, 3: 608-614.*
Sequence alignment, 2016.*
Ausubel et al., "Current Protocols in Molecular Biology", Current Protocols, vol. 2, 1990, Unit 16.5-16.5.4.
Goshima et al., "Human protein factory for converting the transcriptome into an in vitro-expressed proteome", Nature Methods, vol. 5, No. 12, Dec. 2008, pp. 1011-1017.
Inoue et al., "Role of the nucleoplasmin 2 C-terminal domain in the formation of the nucleolus-like bodies in mouse oocytes", The FASEB Journal, vol. 24, No. 2, 2010, pp. 485-494.
International Search Report for PCT/JP2012/080133 mailed on Feb. 12, 2013.
Lechertier et al., "A B23-interacting sequence as a tool to visualize protein interactions in a cellular context", Journal of Cell Science, vol. 120, Pt. 2, 2007, pp. 265-275.
Mori et al., "Tanpakushitsu no Kan'i Seisei o Kano ni suru Fuyoka Tag no Kaihatsu to Riyo", Annual Meeting of the Molecular Biology Society of Japan Program Yoshishu, Nov. 21, 2011, Internet <URL http://www.aeplan.co.jp/mbsj2011/>.
Ohashi et al., "Purification of dihydrofolate reductase-polypeptide fused proteins", Jisedai Sangyo Kiban Gijutsu Symposium Bio Technology Yokoshu, vol. 7, No. 2, 1989, pp. 53-67, Abstract only.
Peng et al., "A system for purification of recombinant proteins in *Escherichia coli* via artificial oil bodies constituted with their oleosin-fused polypeptides", Journal of Biotechnology, vol. 111, No. 1, 2004, pp. 51-57.
Sambrook et al., "Expression of Cloned Genes in *Escherichia coli*", Molecular Cloning, Second Edition, 1989, pp. 17.37-17.41.
Mori et al., "Development and Utilization of the Tag Which Enables to Insolubilize Proteins and Simple Protein Purification", The 34th Annual Meeting of the Molecular Biology Society of Japan; Publication on website: from Nov. 21, 2011 through Apr. 2, 2012.
Goshima et al., "Akusei Shuyo ni Tomonau Shinkeikin Shogai Jiko Kotai Profiling", Gekkan Medical Science Digest, Apr. 25, 2011, vol. 37, No. 4, pp. 132-135, Only the Abstract in English considered.

* cited by examiner

*Primary Examiner* — Ileana Popa
(74) *Attorney, Agent, or Firm* — Birch, Stewart, Kolasch & Birch, LLP

(57) ABSTRACT

A technology which enables a high yield and convenient recovery of a protein and also enables a global protein purification is provided.
A protein tag comprising an amino acid sequence of the full length or a part of MafG protein or an amino acid sequence in which amino acids serving as protease cleavage sites were inserted into the former amino acid sequence is provided. Since this protein tag can impart a high insolubility attributable to MafG protein to a protein to be tagged thereby insolubilizing the tagged protein, the tagged protein can be recovered into an insoluble fraction at a high yield.

12 Claims, 17 Drawing Sheets

SEQ ID NO:2    MRRTLKNRGYAASCRVKRVTQKEELEKQKAELQQEVEKLASEN

ASMKLELDALRSKYEALQTFARTVARSPVAPARGPLAAGLGPLVP

GKVAATSVITIVKSKTDARS

SEQ ID NO:3    MRRTLKNRGYAASCRVKRVTQKEERLEKQKARELQQEVREKLASERN

ASMKLRELDALRSKYEALRQTFARTVARSPVAPARGPLAAGRLGPLVP

RGKVAATRSVITIVRKSKTDARS

SEQ ID NO:4    MRRTLKNRGYARASCRVKRVTQKEERLEKQKARELQRQEVREKLASERN

ASRMKLRELDRALRSKYEALRQTFARTVARSPVRAPARGPLAAGRLGPRLVP

RGKVAATRSVIRTIVRKSKTDARS

Figure 3

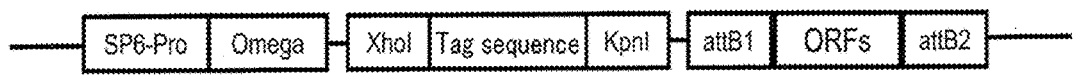

Figure 4

TRIM21
MGLL
CT45A5
Venus
Purified human IgG
Stock fluid    2-Fold-diluted fluid
Figure 13

SEQUENCE LISTING

<160> NUMBER OF SEQ ID NOS: 5

<210> SEQ ID NO 1
<211> LENGTH: 162
<212> TYPE: PRT
<213> ORGANISM: Artificial Sequence
<220> FEATURE:
<223> OTHER INFORMATION: Amid acids sequence of the insoluble tag
      comprising of full sequence of human MafG protein.

<400> SEQUENCE: 1

Met Thr Thr Pro Asn Lys Gly Asn Lys Ala Leu Lys Val Lys Arg Glu
1               5                   10                  15

Pro Gly Glu Asn Gly Thr Ser Leu Thr Asp Glu Glu Leu Val Thr Met
            20                  25                  30

Ser Val Arg Glu Leu Asn Gln His Leu Arg Gly Leu Ser Lys Glu Glu
        35                  40                  45

Ile Val Gln Leu Lys Gln Arg Arg Arg Thr Leu Lys Asn Arg Gly Tyr
    50                  55                  60

Ala Ala Ser Cys Arg Val Lys Arg Val Thr Gln Lys Glu Glu Leu Glu
65              70                  75                  80

Lys Gln Lys Ala Glu Leu Gln Gln Glu Val Glu Lys Leu Ala Ser Glu
                85                  90                  95

Asn Ala Ser Met Lys Leu Glu Leu Asp Ala Leu Arg Ser Lys Tyr Glu
            100                 105                 110

Ala Leu Gln Thr Phe Ala Arg Thr Val Ala Arg Ser Pro Val Ala Pro
        115                 120                 125

Ala Arg Gly Pro Leu Ala Ala Gly Leu Gly Pro Leu Val Pro Gly Lys
    130                 135                 140

Val Ala Ala Thr Ser Val Ile Thr Ile Val Lys Ser Lys Thr Asp Ala
145                 150                 155                 160

Arg Ser

<210> SEQ ID NO 2
<211> LENGTH: 107
<212> TYPE: PRT
<213> ORGANISM: Artificial Sequence
<220> FEATURE:
<223> OTHER INFORMATION: Amid acids sequence of the insoluble tag
      comprising of partial sequence of human MafG protein.

<400> SEQUENCE: 2

Arg Arg Thr Leu Lys Asn Arg Gly Tyr Ala Ala Ser Cys Arg Val Lys
1               5                   10                  15

Arg Val Thr Gln Lys Glu Glu Leu Glu Lys Gln Lys Ala Glu Leu Gln
            20                  25                  30

Gln Glu Val Glu Lys Leu Ala Ser Glu Asn Ala Ser Met Lys Leu Glu
        35                  40                  45

Leu Asp Ala Leu Arg Ser Lys Tyr Glu Ala Leu Gln Thr Phe Ala Arg
    50                  55                  60

Thr Val Ala Arg Ser Pro Val Ala Pro Ala Arg Gly Pro Leu Ala Ala
65              70                  75                  80

Gly Leu Gly Pro Leu Val Pro Gly Lys Val Ala Ala Thr Ser Val Ile
                85                  90                  95

Thr Ile Val Lys Ser Lys Thr Asp Ala Arg Ser
            100                 105

<210> SEQ ID NO 3
<211> LENGTH: 117
<212> TYPE: PRT
<213> ORGANISM: Artificial Sequence
<220> FEATURE:
<223> OTHER INFORMATION: Amid acids sequence of the insoluble tag
      comprising of partial sequence of human MafG protein and insertion
      of 10 arginines.

<400> SEQUENCE: 3

Arg Arg Thr Leu Lys Asn Arg Gly Tyr Ala Ala Ser Cys Arg Val Lys
1               5                   10                  15

Arg Val Thr Gln Lys Glu Glu Arg Leu Glu Lys Gln Lys Ala Arg Glu
            20                  25                  30

Leu Gln Gln Glu Val Arg Glu Lys Leu Ala Ser Glu Arg Asn Ala Ser
        35                  40                  45

Met Lys Leu Arg Glu Leu Asp Ala Leu Arg Ser Lys Tyr Glu Ala Leu
    50                  55                  60

Arg Gln Thr Phe Ala Arg Thr Val Ala Arg Ser Pro Val Ala Pro Ala
65                  70                  75                  80

Arg Gly Pro Leu Ala Ala Gly Arg Leu Gly Pro Leu Val Pro Arg Gly
                85                  90                  95

Lys Val Ala Ala Thr Arg Ser Val Ile Thr Ile Val Arg Lys Ser Lys
                100                 105                 110

Thr Asp Ala Arg Ser
        115

<210> SEQ ID NO 4
<211> LENGTH: 124
<212> TYPE: PRT
<213> ORGANISM: Artificial Sequence
<220> FEATURE:
<223> OTHER INFORMATION: Amid acids sequence of the insoluble tag
      comprising of partial sequence of human MafG protein and insertion
      of 17 arginines

<400> SEQUENCE: 4

Arg Arg Thr Leu Lys Asn Arg Gly Tyr Ala Arg Ala Ser Cys Arg Val
1               5                   10                  15

Lys Arg Val Thr Gln Lys Glu Glu Arg Leu Glu Lys Gln Lys Ala Arg
            20                  25                  30

Glu Leu Gln Arg Gln Glu Val Arg Glu Lys Leu Ala Ser Glu Arg Asn
        35                  40                  45

Ala Ser Arg Met Lys Leu Arg Glu Leu Asp Arg Ala Leu Arg Ser Lys
    50                  55                  60

Tyr Glu Ala Leu Arg Gln Thr Phe Ala Arg Thr Val Ala Arg Ser Pro
65                  70                  75                  80

Val Arg Ala Pro Ala Arg Gly Pro Leu Ala Ala Gly Arg Leu Gly Pro
                85                  90                  95

Arg Leu Val Pro Arg Gly Lys Val Ala Ala Thr Arg Ser Val Ile Arg
                100                 105                 110

Thr Ile Val Arg Lys Ser Lys Thr Asp Ala Arg Ser
        115                 120

<210> SEQ ID NO 5
<211> LENGTH: 489
<212> TYPE: DNA
<213> ORGANISM: Homo sapiens

<400> SEQUENCE: 5
atgacgaccc ccaataaagg aaacaaggcc ttgaaggtga agcgggagcc gggtgagaat      60
ggcaccagcc tgacggatga ggagctggtg accatgtcgg tgcgggagct gaaccagcac     120
ctgcggggcc tgtccaagga ggagatcgtc cagctgaagc agcgccggcg cacgctcaag     180
aaccgcggct acgctgccag ctgccgcgtg aagcgggtga cgcagaagga ggagctggag     240

```
aagcagaagg cggagctgca gcaggaggtg gagaagctgg cctcagagaa cgccagcatg    300
aagctggagc tcgacgcgct gcgctccaag tacgaggcgc tgcagaccttc cgcccggacg    360 gtggcccgca gccccgtggc gccagcccgg ggcccccttg ccgccggcct ggggcccctc    420
gtcccaggca aggtggccgc caccagcgtc atcacaatag taaagtccaa gacggatgcc    480
cgatcgtat                                                            489
```

PROTEIN TAG, TAGGED PROTEIN, AND PROTEIN PURIFICATION METHOD

TECHNICAL FIELD

The present invention relates to a protein tag, tagged protein, protein purification method, and the like. More particularly, it relates to a protein tag which insolubilizes a recombinant protein thereby enabling a convenient recovery and the like.

BACKGROUND ART

Conventionally, a recombinant protein is purified by allowing a target protein to be expressed as a fusion protein with an affinity tag and utilizing a specific affinity between the affinity tag and other molecule to thereby isolating the fusion protein from a soluble fraction. The affinity tag serves also to increase the solubility of the target protein to allow the fusion protein to be expressed as solubilized.

A commonly employed affinity tag may for example be His tag (histidine tag), GST tag (glutathione-S-transferase tag), MBP tag (maltose-binding protein tag), and FLAG tag. The His tag is a peptide containing about 6 to 10 histidine residues and specifically binds to a metal ion such as nickel ion. The GST tag and the MBP tag specifically bind to low molecular weight compounds such as glutathione and maltose, respectively.

For example, a solution of a protein tagged with the His tag is allowed to pass through a chelate resin having nickel ions immobilized thereon, onto which it is thus adsorbed. Subsequently, the nickel ion or a low molecular weight compound capable of binding to the nickel ion such as imidazole is allowed to pass through the resin, thereby allowing the fusion protein once adsorbed to be eluted and recovered.

The FLAG tag is a tag (epitope tag) utilizing an antigen-antibody reaction, and a protein tagged with the FLAG tag can be isolated from the soluble fraction by allowing it to bind to an anti-FLAG antibody. The epitope tag may otherwise be myc tag and HA tag, and the aforementioned His tag and GST tag can also be employed as epitope tags.

Such an affinity tag is designed also for allowing the fusion protein to be cleaved into a target protein and the tag upon a protease treatment thereby separating the tag from the target protein. For example, a fusion protein once adsorbed onto a resin via a tag is subjected to a protease treatment to separate the target protein and the tag from each other thereby allowing the target protein to be released and recovered exclusively from the resin.

Patent Document 1 discloses a technology for reacting a protein, which was labeled with a composite tag consisting of a His tag and a FLAG tag, specifically with a nickel-binding carrier and an anti-FLAG antibody-binding carrier thereby accomplishing separation and purification of the protein. Patent Document 2 also describes a method for recovering a target protein by using a peptide chain, which contains a cellulose-binding region of a cellulase, as an affinity tag and conduct a protease treatment to separate the tag from the fusion protein.

CITATION LIST

Patent Literature

[Patent Document 1] JP-A No. 2003-292500
[Patent Document 2] JP-A No. 1106-277088

Non-Patent Literature

[Non-Patent Document 1] "Human protein factory for converting the transcriptome into an in vitro-expressed proteome." Goshima, N., et al., Nature Methods. 2008, Vol. 5, No. 12, p. 1011-1017
[Non-Patent Document 2] "Molecular Cloning, SECOND EDITION", 1989, 17.37-17.41, Cold Spring Harbor Laboratory Press
[Non-Patent Document 3] "CURRENT PROTOCOLS IN MOLECULAR BIOLOGY", 1990, Vol. 2 UNIT 16.5-16.5.4 CURRENT PROTOCOLS

SUMMARY OF INVENTION

Technical Problem

Since the protein purification of the prior art which employs an affinity tag isolates a fusion protein from a soluble fraction utilizing the specific affinity of the affinity tag, the fusion protein should be expressed in a soluble state and partitioned into the soluble fraction. It is also required that the affinity tag in the fusion protein retains its specific affinity with other molecules.

Nevertheless, some of target proteins are difficult to be solubilized, and the % solubilizability may vary substantially among proteins. In addition, the affinity tag in a fusion protein may sometimes be unsuccessful in exerting its affinity with other molecules sufficiently under the influence of the effect of the target protein.

Accordingly, in the protein purification of the prior art using the affinity tag, the protein yield depends on the solubility level (% solubilizability) of the fusion protein and the affinity level (% retained affinity) of the affinity tag, and the yield may sometime be extremely low. Also in the purification of the prior art, it is difficult to synthesize and purify numerous proteins globally regardless of their % solubilizabilities and the % retained affinities.

Accordingly, a major object of the present invention is to provide a technology which enables a high yield and convenient recovery of a protein and also enables a global protein purification.

Solution to Problem

When recombinant proteins are expressed, some become soluble and others become insoluble, depending on the type of the proteins to be expressed. Moreover, even a single type of the protein may sometimes be separated into 2 fractions, one being soluble fraction and the other being insoluble fraction.

As a result of our intensive studies, an insolubilizing tag was found, which insolubilizes expressed proteins regardless of the type of the proteins, and which allows the expressed proteins to be purified and recovered uniformly from the insoluble fraction. In addition, it was also found that the insolubilizing tag according to the present invention can be solubilized again by a surfactant, which is contained in a solvent for solubilizing a protein of an inclusion body, at a concentration lower than an ordinary concentration.

To overcome the problems described above, the present invention provides a protein tag comprising an amino acid sequence of the full length or a part of MafG protein or an amino acid sequence in which amino acids serving as protease cleavage sites were inserted into the former amino acid sequence.

According to this protein tag, a high insolubility attributable to MafG protein can be imparted to a protein to be tagged.

In this protein tag, the amino acid serving as a protease cleavage site may be arginine which is a trypsin cleavage site.

This protein tag typically comprises the amino acid sequence represented by SEQ ID NO:1 to 4.

Also the present invention provides a protein tagged with a protein tag comprising an amino acid sequence of the full length or a part of MafG protein or an amino acid sequence in which amino acids serving as protease cleavage sites were inserted into the former amino acid sequence.

This tagged protein can be utilized as a protein array formed by immobilizing a protein on a support.

Furthermore, the present invention provides a peptide obtained by a protease treatment of a protein tagged with a protein tag comprising an amino acid sequence in which an amino acid serving as protease cleavage sites were inserted into an amino acid sequence of the full length or a part of MafG protein.

Since the peptide obtained by a protease treatment of a protein tagged with a protein tag comprising an amino acid sequence in which an amino acid serving as protease cleavage sites were inserted can be designed in such a manner that the peptide derived from the tag can extremely be short, it is used preferably as standard peptides for mass spectrometry with regard to the protein subjected to the mass spectrometry.

Furthermore, the present invention provides a vector which expresses the aforementioned protein tag. This vector expresses a fusion protein between a target protein to be tagged and the protein tag.

Furthermore, the present invention provides a protein purification method comprising: a fusion protein preparation procedure for tagging a target protein with a protein tag comprising an amino acid sequence of the full length or a part of MafG protein or amino acids sequences in which amino acids serving as protease cleavage sites were inserted into the former amino acid sequence; and, a purification procedure for recovering the aforementioned target protein which has been tagged into an insoluble fraction.

Since the aforementioned protein tag allows a high insolubility attributable to MafG protein to be imparted to a target protein and allows the fusion protein to be insolubilized, the fusion protein can be recovered into the insoluble fraction at a high yield.

In this protein purification method, the aforementioned fusion protein preparation procedure is a procedure in which a vector expressing a fusion protein between the aforementioned target protein and the aforementioned protein tag is employed in a cell-free protein synthesis system (for example, wheat cell-free protein synthesis system) or a cell-associated protein synthesis system to synthesis the fusion protein. In addition, the aforementioned purification procedure is a procedure for centrifuging the aforementioned target protein which has been tagged.

Moreover, the present invention provides a method for purifying an antibody to a protein, the antibody purification method comprising using a fusion protein between the protein and a protein tag comprising an amino acid sequence of the full length or a part of MafG protein or an amino acid sequence in which amino acids serving as protease cleavage sites were inserted into the former amino acid sequence.

Advantageous Effects of Invention

According to the present invention, a technology which enables a high yield and convenient recovery of a protein and also enables a global protein purification is provided.

BRIEF DESCRIPTION OF DRAWINGS

FIG. 3 is a view illustrating the design of the protease cleavage sites in an insolubilizing tag.

FIG. 4 is a view illustrating a fundamental sequence of a vector according to the invention.

FIG. 13 is a drawing-substituting photograph showing the results of the detection of the autoantibody using the protein array made in Example 4 (Example 5).

DESCRIPTION OF EMBODIMENTS

Figure 1:
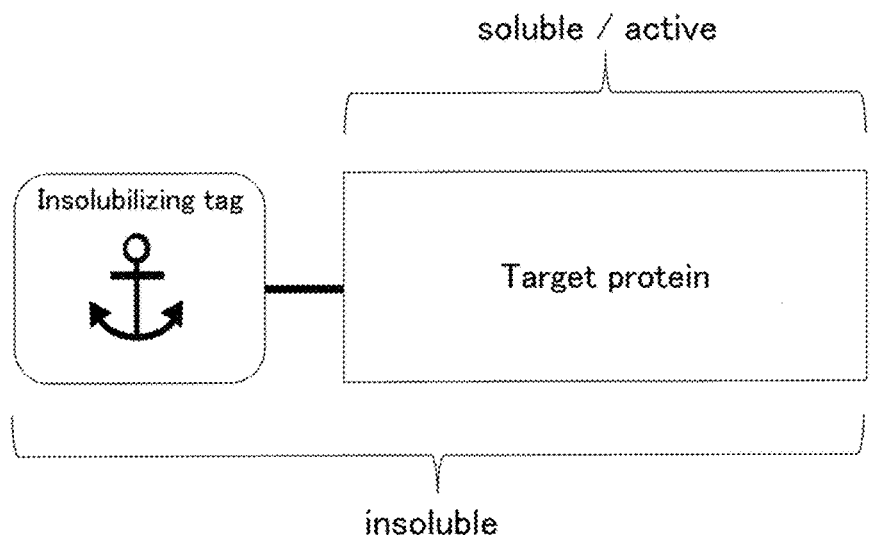
FIG. 1 is a view illustrating a protein tag (insolubilizing tag) and a tagged protein according to the invention.

Preferred embodiments of the present invention are described below with referring to the drawings. These embodiments are merely examples representing the present invention, and are not intended to allow the scope of the present invention to be interpreted narrowly. The description is made in the following order.
1. Protein tag
(1-1) Insolubilizing tag
(1-2) Designing of protease cleavage site
2. Protein purification method
(2-1) Fusion protein preparation procedure
(2-1-1) Vector
(2-1-2) Expression system
(2-2) Purification procedure
3. Tagged protein and its utilization
(3-1) Tagged protein
(3-2) Standard peptide for mass spectrometry
(3-3) Antibody purification
1. Protein Tag
(1-1) Insolubilizing Tag We employed a cell-free expression system (wheat germ cell-free system) to search for a highly insoluble protein globally. As a result, MafG protein was identified. MafG protein was found to have completely no solubility even when being expressed as a fusion protein with a solubilizing tag employed conventionally such as His tag, GST tag, and the like. MafG protein is one of transcription factors and consists of an amino acid sequence having 162 residues (SEQ ID NO:1). The base sequence of the coding region of MafG gene is represented by SEQ ID NO:5.

The protein tag according to the present invention comprises the full length or a part of the amino acid sequence of the aforementioned MafG protein. This protein tag constituted by comprising the full length or a part of the amino acid sequence of MafG protein imparts a high insolubility attributable to MafG protein to a protein to be tagged. Thus, the protein tag according to the present invention serves as "an insolubilizing tag" which is tagged to a soluble protein, thereby insolubilizing the whole tagged protein integrally (see FIG. 1). We also observed that even when a protein such as various enzymes such as kinase or phosphatase or fluorescent protein is expressed as a fusion protein with this insolubilizing tag the fusion protein retains the enzymatic activity or the fluorescence (see Example 2).

The amino acid sequence of MafG protein contained in the insolubilizing tag may be the entire sequence or a partial sequence of the amino acid sequence of MafG protein as long as MafG protein can retain a high insolubility. When a partial sequence is employed, then the partial sequence may be any portion of the full length of the amino acid sequence of MafG protein, and the number of the amino acid residues of the partial sequence is not limited particularly. In addition, the insolubilizing tag may have an amino acid sequence of any number of the residues in addition to the full length or a part of the amino acid sequence of MafG protein at its N terminal or C terminal, as long as it can retain the high insolubility exhibited by MafG protein.

In addition, the amino acid sequence of MafG protein contained in the insolubilizing tag is not limited to the amino acid sequence of human MafG protein (SEQ ID NO:1), and may be an amino acid sequence of the homolog of other species such as mouse or rat.

A typical amino acid sequence of the insolubilizing tag may for example be the amino acid sequence represented by SEQ ID NO:1. This amino acid sequence is identical to the full length of the amino acid sequence of human MafG protein. In addition, the amino acid sequence of the insolubilizing tag may be an amino acid sequence formed by adding 1 or 2 or more amino acids to the N terminal or C terminal of the amino acid sequence represented by SEQ ID NO:1.

In addition, the typical amino acid sequence of the insolubilizing tag may for example be the amino acid sequence represented by SEQ ID NO:2. This amino acid sequence is a partial sequence of human MafG protein, and corresponds to the 56th to 162nd residues from the N terminal of the full length. We observed that the portion of the 56th to 162nd residues from the N terminal in human MafG protein is attributable to the insolubility (see Test Example 1). In addition, the amino acid sequence of the insolubilizing tag may be an amino acid sequence formed by adding 1 or 2 or more amino acids to the N terminal or C terminal of the amino acid sequence represented by SEQ ID NO:2.

(1-2) Designing of Protease Cleavage Site

Figure 2:
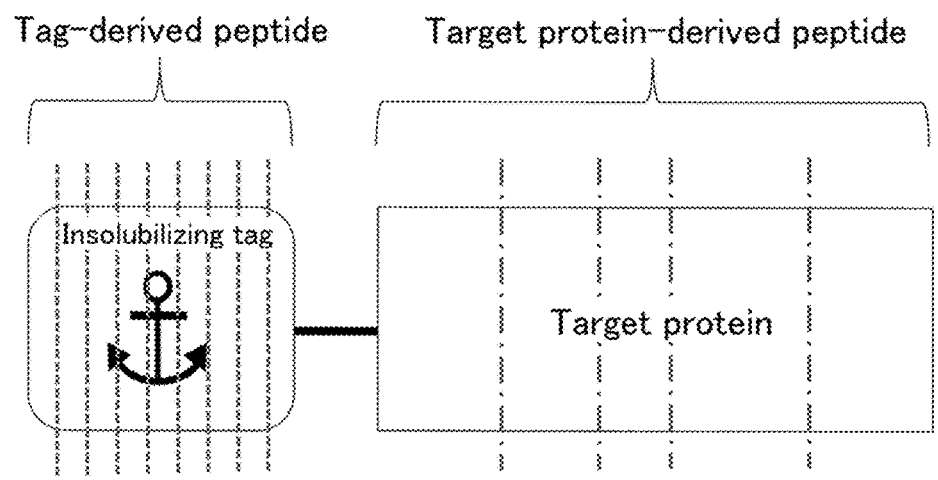
FIG. 2 is a view illustrating an insolubilizing tag and the protease cleavage site of a tagged protein.

The insolubilizing tag according to the present invention, for the purpose of utilizing the tagged protein in the preparation of the standard peptide for mass spectrometry described below, preferably comprises an amino acid sequence in which amino acids serving as protease cleavage sites were inserted into the full length or a part of the amino acid sequence of MafG protein. FIG. 2 is a schematic view illustrating the protease cleavage sites of the insolubilizing tag and the tagged protein. The cleavage sites designed in the amino acid sequence of the insolubilizing tag are indicated with the dotted line, while the cleavage sites within the amino acid sequence of the target protein are indicated with the one-dot line. The cleavage sites in the insolubilizing tag indicated with the dotted line include both of the cleavage sites within MafG protein and newly provided cleavage sites.

The amino acid to be inserted can appropriately be selected depending on the type of the protease. For example, when using trypsin which has a cleavage specificity on the side of the carboxyl group of lysine and arginine, lysine or arginine is inserted. The proteases which may be used in addition to trypsin are Lys-C, Glu-C, Asp-N, chymotrypsin, V8, and the like.

While the position at which the amino acids serving as protease cleavage sites to be inserted into the full length or a part of the amino acid sequence of MafG protein is inserted is not limited particularly, it is preferable that the insertion is at a position allowing the length of the tag-derived peptide obtained after protease treatment to be 6 residues or less. Similarly, the number of the insertions of the amino acids serving as cleavage sites is not limited.

When the protease is trypsin, a preferable amino acid sequence of the insolubilizing tag may for example be the amino acid sequence represented by SEQ ID NO:3 (see FIG. 3). The amino acid sequence represented by SEQ ID NO:3 is a sequence in which 10 residues of arginine were inserted into the amino acid sequence represented by SEQ ID NO:2, and is a sequence obtained by altering the amino acid sequence represented by SEQ ID NO:2 so that the number of the amino acids between arginine and arginine becomes 6 residues or less. In the amino acid sequence shown in FIG. 3, an underlined "R" represents arginine within wild-type MafG protein, while an arrowed "R" represents arginine which was inserted additionally (10 in total).

Also, the amino acid sequence represented by SEQ ID NO:4 is the amino acid sequence in which 17 residues of arginine were inserted into the amino acid sequence represented by SEQ ID NO:2, and is a sequence obtained by alteration for further reducing the number of the amino acids between arginine and arginine when compared with the amino acid sequence represented by SEQ ID NO:3. In the amino acid sequence shown in FIG. 3, an arrowed "R" represents arginine which was further inserted additionally into the amino acid sequence represented by SEQ ID NO:3 (7 in total).

2. Protein Purification Method (2-1) Fusion Protein Preparation Procedure

The protein purification method using the aforementioned insolubilizing tag is described. The protein purification method includes a fusion protein preparation procedure and a purification procedure.

In the fusion protein preparation procedure, a target protein to be purified is prepared as a fusion protein with an insolubilizing tag. The fusion protein is obtained by ligating a target protein-encoding DNA sequence to an insolubilizing tag-encoding DNA sequence, and introducing a vector constituted so that the target protein can be expressed as a fusion protein with the insolubilizing tag into expression system.

(2-1-1) Vector

FIG. 4 shows an example of the fundamental sequence of the vector. The vector shown in the figure has a constitution in which the amino acid sequence of the insolubilizing tag-encoding DNA sequence (tag sequence) is located upstream (5' side) of the position at which the amino acid sequence-encoding cDNA of the target protein is inserted (open reading frames (ORFs)). Further upstream of the tag sequence, a transcription promoter sequence and a translation enhancer sequence are positioned. The transcription promoter sequence and the translation enhancer sequence which are exemplified here are SP6 promoter sequence and omega sequence employed frequently in a wheat cell-free protein synthesis system, respectively, to which they are not limited. It is also possible to ligate the tag sequence downstream (3' side) of the ORFs. Thus, the insolubilizing tag can be used as an N-terminal or a C-terminal tag.

Around the tag sequence and the ORFs, a sequence for gene recombination may be provided. An example illustrated here has a restriction enzyme XhoI site upstream of the tag sequence and a KpnI site positioned downstream, as well as an attB1 site upstream of ORFs and attB2 positioned downstream.

(2-1-2) Expression System

As an expression system, a cell-free system or a cell-associated system can be employed, and a wheat cell-free expression system can especially be employed. Otherwise, the protein synthesis system of the cell-free system may for example be those of E. coli, insects, rabbit reticulocyte, and the like. The protein synthesis system of the cell-associated system may for example be those of E. coli, mammalian cells, insect cells, yeast, and the like.

Figure 5:
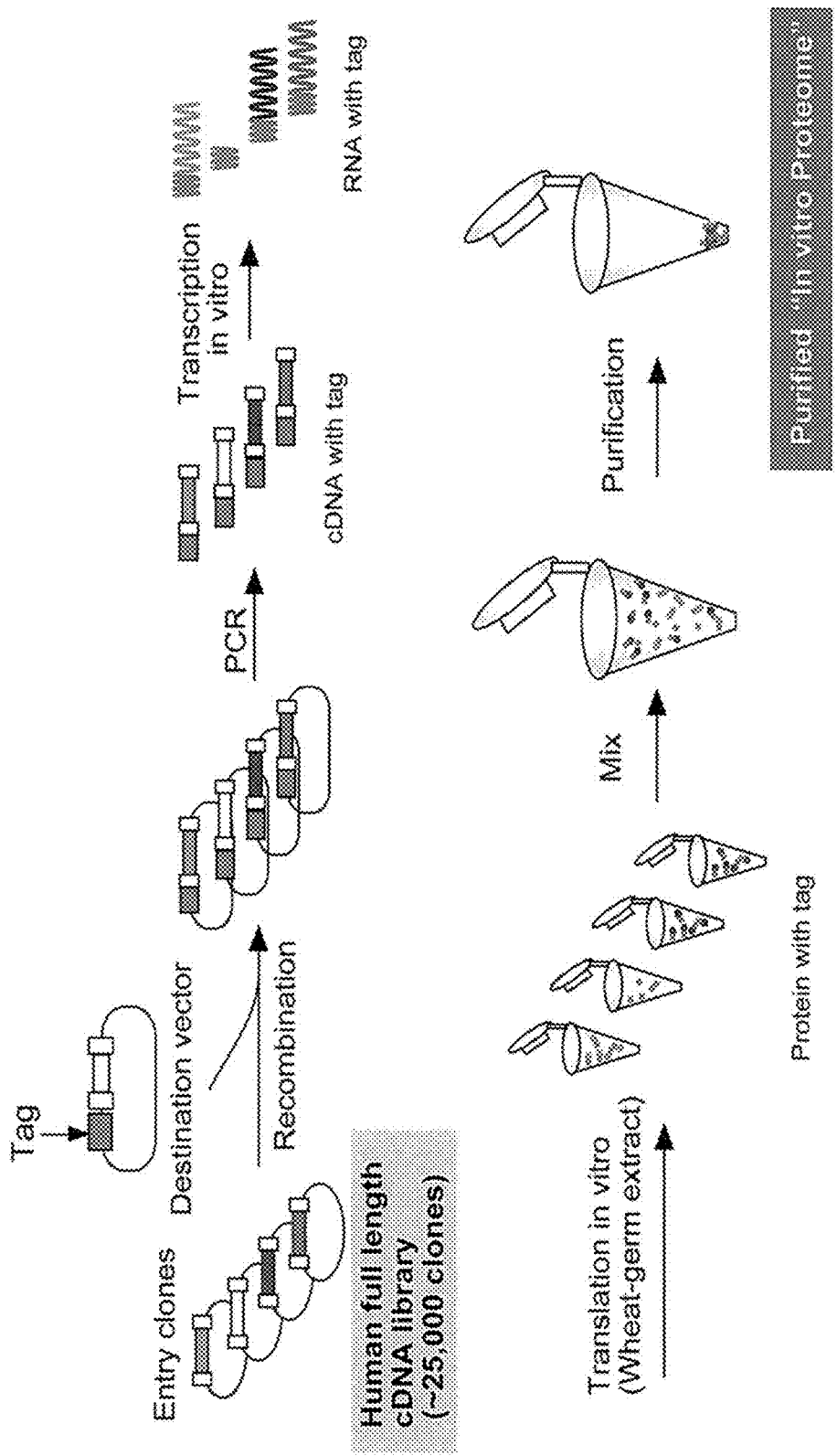
FIG. 5 is a view illustrating an example of the procedure of the protein purification method according to the invention.

When expressing a fusion protein in a cell-free system, first the aforementioned vector is subjected to a nucleic acid amplification such as PCR to amplify the target protein and protein tag-encoding DNA sequence (tagged cDNA). Then, from the tagged cDNA, an RNA (tagged RNA) is transcribed by in vitro transcription. Thereafter, the tagged RNA, in the form of a mixture fluid with the wheat cell extract, is subjected to an in vitro translation (see FIG. 5).

It is also possible to use, as a protein synthesis system of the cell-associated system, a known system employing E. coli, insect cells, and mammalian cell. Introduction of a gene into a cell can be conducted according to a known transfection method such as calcium phosphate method, electroporation, lipofection, microinjection, and the like.

(2-2) Purification Procedure

Subsequently, in a purification procedure, the target protein expressed as a fusion protein with the insolubilizing tag is recovered into an insoluble fraction. The target protein tagged with the insolubilizing tag is insolubilized integrally as a whole tagged protein. Accordingly, by centrifuging the mixture fluid after the in vitro translation in the cell-free expression system or the cell lysis fluid in the cell-associated expression system, the target protein can be pelleted down into an insoluble fraction, thereby accomplishing the recovery easily (see FIG. 5).

While the centrifugation can be conducted according to an ordinary method, a condition can be exemplified which employs 15,000×g, 20 minutes, and 4° C. In order to prevent migration of a soluble protein as a contaminant protein into the insoluble fraction, it is preferable that a surfactant such as Tween 20 is added to the solution subjected to the centrifugation.

It is also possible to use a filter to recover the target protein tagged with the insolubilizing tag into a filter cake fraction. The mixture fluid after the in vitro translation in the cell-free expression system or the cell lysis fluid in the cell-associated expression system are allowed to pass through a filter having a pore size of about 0.22 μm. As a result, the soluble protein which passes through the filter and the target protein which is trapped on the filter can be separated.

The insolubilizing tag according to the present invention can impart a high insolubility attributable to MafG protein to the target protein to be tagged, and, even a highly soluble target protein can be insolubilized integrally as a whole tagged protein. Accordingly, the protein purification method employing this insolubilizing tag enables, unlike to a method of the prior art employing an affinity tag, purification of the target protein at a high yield independently of the solubility level (% solubilizability) thereof.

Also in the protein purification method according to the present invention, the tagged target protein can be recovered by a convenient means such as centrifugation. Accordingly, this method enables, unlike to a method of the prior art employing an affinity tag, purification of the target protein at a high yield anytime regardless of the affinity level (% retained affinity) of the tag in the fusion protein.

In addition, the protein purification method according to the present invention enables purification even of a protein which was difficult to be purified by a method of the prior art due to low % solubilizability or % retained affinity, resulting in a possibility of global synthesis and purification of numerous proteins regardless of the % solubilizability or % retained affinity thereof.

The insolubilizing tag protein thus recovered can be solubilized by treatment with a surfactant, treatment with a protein denaturing agent 7M guanidine hydrochloride or 7M urea, or using acid or alkaline solution. Also, the tagged protein according to the present invention can be solubilized in the presence of sodium dodecyl sulfate (SDS) at a concentration of 0.04 to 1% (w/v) (see Test Examples 3 and 4).

Generally, the protein once insolubilized is solubilized again frequently by using a chaotropic salt having a high denaturing activity such as guanidine hydrochloride (Non-patent Document 2, Non-patent Document 3), or by using an SDS buffer containing 2% SDS or reducing agent for SDS-PAGE. Nevertheless, in a solvent containing the chaotropic salt or surfactant at a high concentration, the target protein may be denatured, and, if the target protein is an enzyme, the enzymatic activity may not be retained. Also in order to use a protein, which was solubilized by a solvent containing the chaotropic salt or surfactant at a high concentration, in a biochemical assay and the like while adding an enzyme such as a protease, it is required to reduce the concentration of the chaotropic salt or surfactant in the solvent by means of dilution, dialysis, ultrafiltration, and the like.

On the contrary, the tagged protein according to the present invention can be solubilized by SDS at a concentration for example of 0.04 to 1% (w/v). As a result, the tagged protein recovered into the insolubilized fraction can be used in the subsequent procedure without conducting complicated operations such as dilution, dialysis, ultrafiltration, and the like. The subsequent procedure means, for example, a protease treatment procedure in utilizing the tagged protein as a standard peptide for mass spectrometry or a procedure for binding the tagged protein to a protein array substrate, as described below.

3. Tagged Protein and its Utilization (3-1) Tagged Protein

The tagged protein according to the present invention is obtained by the aforementioned protein purification method, and characterized by being tagged with an insolubilizing tag. The tagged protein has an insolubilizing tag ligated at least one of the N-terminal and the C-terminal of the target protein, depending on the structure of the vector employed.

Also the tagged protein according to the present invention can be solubilized from the state exhibiting the insolubility as described above. Accordingly, the present invention may also be a protein production method comprising: a fusion protein preparation procedure for tagging a target protein with a protein tag comprising an amino acid sequence of the full length or a part of MafG protein or an amino acid sequence in which amino acids serving as protease cleavage sites were inserted into the former amino acid sequence; a purification procedure for recovering the aforementioned target protein which has been tagged into an insoluble fraction; and a solubilization procedure for allowing the tagged target protein once recovered in the insoluble fraction to be solubilized again in a solvent. The solvent preferably contains SDS at a concentration of 0.04 to 1% (w/v).

According to the insolubilizing tag according to the present invention, numerous proteins can be synthesized and purified regardless of its % solubilizability and % retained affinity. Accordingly, by inserting a commercially available cDNA library into ORFs of a vector to make an expression clone library and conducting the protein expression and purification, a global protein library (in vitro proteome) can be prepared.

The protein library prepared as an in vitro proteome can be utilized for example in a protein array. A protein is solubilized using a surfactant such as sodium dodecyl sulfate (SDS), a denaturing agent such as guanidine hydrochloride or urea, or an acid or alkaline solution and then immobilized on a support such as a nitrocellulose membrane, and various array substrates to produce a protein array. The protein array can be utilized for example in screening autoantibodies in a serum.

(3-2) Standard Peptide for Mass Spectrometry

The tagged protein according to the present invention can be utilized in producing a standard peptide for mass spectrometry (internal standard peptide). In LC/MS/MS (Liquid chromatography/mass spectrometry/mass spectrometry), CE/MS/MS (capillary electrophoresis/mass spectrometry/mass spectrometry), and GC/MS/MS (gas chromatography/mass spectrometry/mass spectrometry), an analysis referred to as a selected reaction monitoring (SRM) and a multiple reaction monitoring (MRM) is conducted. Since SRM and MRM have extremely high specificities, they are excellent in quantifying ultratrace ingredients.

Figure 6:
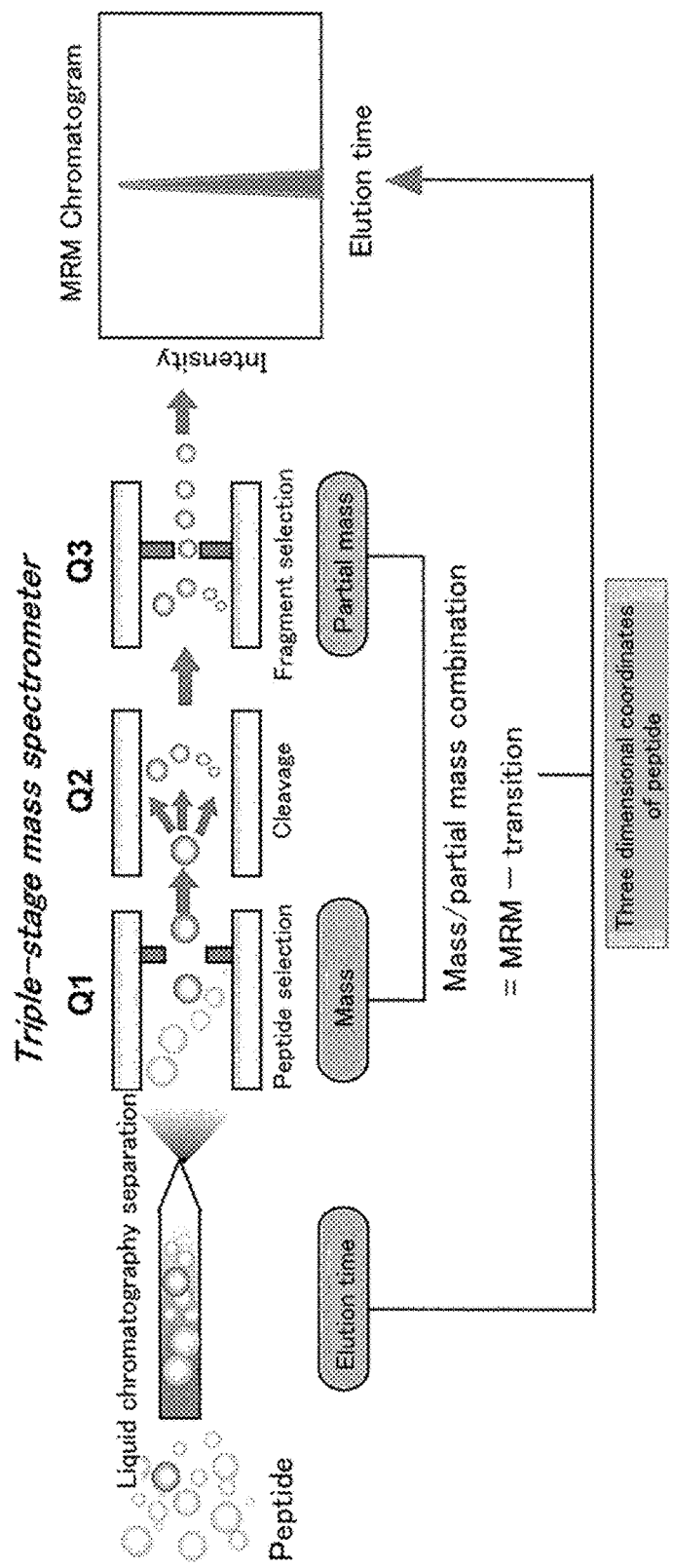
FIG. 6 is a view illustrating the principle of the measurement of a multiple reaction monitoring (MRM).

FIG. 6 shows the principle of measurement of ordinary MRM. In MRM, first, various ions ionized with ionization probes are subjected to the selection of a certain ion (precursor ion) in Q1 (first mass spectrometer). Then, the precursor ion is broken (collision-induced dissociation) in a collision cell (Q2) and a certain ion is detected from the broken ions (product ions) in Q3 (second mass spectrometer).

In MRM, multiple channels can be set in a single measurement, and certain types of proteins can exclusively detected from crude proteins (a crudely purified product) and quantified. The quantification of proteins by MRM can be accomplished by determining the absolute amount of a quantification target peptide based on the peak area ratio between the quantification target peptide and the internal standard stable isotope-labeled peptide together with the calibration curve.

For the purpose of a highly accurate quantification, a peptide having a high ionization efficiency should preliminarily be selected as an internal standard peptide from peptides produced from the protein which is the quantification target. Since the selection of the internal standard peptide is conducted by an actual measurement of the protein which is the quantification target while observing the MS/MS spectrum, a quantification target protein which has been purified for the actual measurement should be ready to use.

Also, the internal standard peptide is subjected to the measurement as being labeled with a stable isotope which enables differentiation from peptides derived from the quantification target protein in a crudely purified product (sample) of the proteins and also as being mixed with the sample. Therefore, it is required for MRM to make the internal standard peptide ready to use upon each measurement.

Since the tagged protein according to the present invention enables synthesis and purification of any protein regardless of the % solubilizability of the protein or the % retained affinity of the fusion protein, it can be utilized preferably as a protein for selecting the aforementioned internal standard peptide and as a protein for preparing the internal standard peptide. Thus, by subjecting a purified tagged protein to protease treatment and then to analysis by LC/MS/MS, an optimal internal standard peptide for MRM can be selected. Moreover, the protease treatment can be conducted while the tag is still being attached without removing the tag preliminarily from the tagged protein. Therefore, there is no need of operation for removing the tag once attached for purification from the purified tagged protein. In addition, the peptide mixture obtained by the protease treatment of the tagged protein labeled with the stable isotope can itself be utilized as an internal standard peptide for MRM.

When using the tagged protein according to the present invention as an internal standard peptide for MRM and the like, a less number of the amino acid residues constituting the protein tag is preferred. A larger number of the amino acid residues constituting the protein tag tends to give longer peptides contained in the protease digestion product, which allows the peptides detected in the mass spectrometry to interfere with the measurement of the target protein more easily. Therefore, it is preferable to use, as a protein tag, a portion containing SEQ ID NO:2 which is involved in the insolubility in the amino acid sequence of MafG protein. By using the amino acid sequence represented by SEQ ID NO:2 as a tag, the number of the amino acid residues of the protein tag can be reduced while retaining the insolubility of the protein tag.

Moreover, a tagged protein synthesized and purified using, as an insolubilizing tag, one which contains an amino acid sequence in which amino acids serving as protease cleavage sites were inserted into the full length or a part of the amino acid sequence of MafG protein (see SEQ ID NO:3, 4) can preferably be utilized.

The amino acids serving as protease cleavage sites have been inserted at the position allowing the length of the peptide obtained after the protease treatment as being derived from the insolubilizing tag (tag-derived peptide) to be 6 residues or less (see FIG. 2). By ensuring that the length of the insolubilizing tag-derived peptide obtained after the protease treatment is 6 residues or less, it is possible, in the internal standard peptide obtained by the protease treatment of the tagged protein, to distinguish the tag-derived peptide from the protein-derived peptide clearly. As a result, the risk that the tag-derived peptide is selected mistakenly as an internal standard peptide or that the tag-derived peptide serves as a noise during MRM measurement can be prevented.

For example, when using trypsin as a protease, the amino acid to be inserted into the amino acid sequence of the protein tag according to the present invention is preferably arginine or lysine. A larger amount of arginine or lysine serving as trypsin cleavage sites in the amino acid sequence of the protein tag results in a shorter length of the peptide derived from the protein tag. On the other hand, insertion of arginine or lysine which is a hydrophilic amino acid into an insoluble protein tag may results in a change in the characteristics of the protein tag.

Especially when the number of the arginine residues to be inserted into a tag protein consisting of 107 amino acid residues represented by SEQ ID NO:2 is less than 17, the length of the tag protein-derived peptide can be shorter while retaining the insolubility of the tag protein. Accordingly, the protein tag whose number of the arginine residues inserted into the amino acid sequence represented by SEQ ID NO:2 is less than 17 is employed preferably as a tag for use in purification of an internal standard peptide in mass spectrometry. Specifically, the number of the arginine residues inserted into the amino acid sequence represented by SEQ ID NO:2 is preferably 1 to 16, and especially 6 to 10.

(3-3) Antibody Purification

Also, the tagged protein according to the present invention can be utilized in antibody purification.

Figure 7:
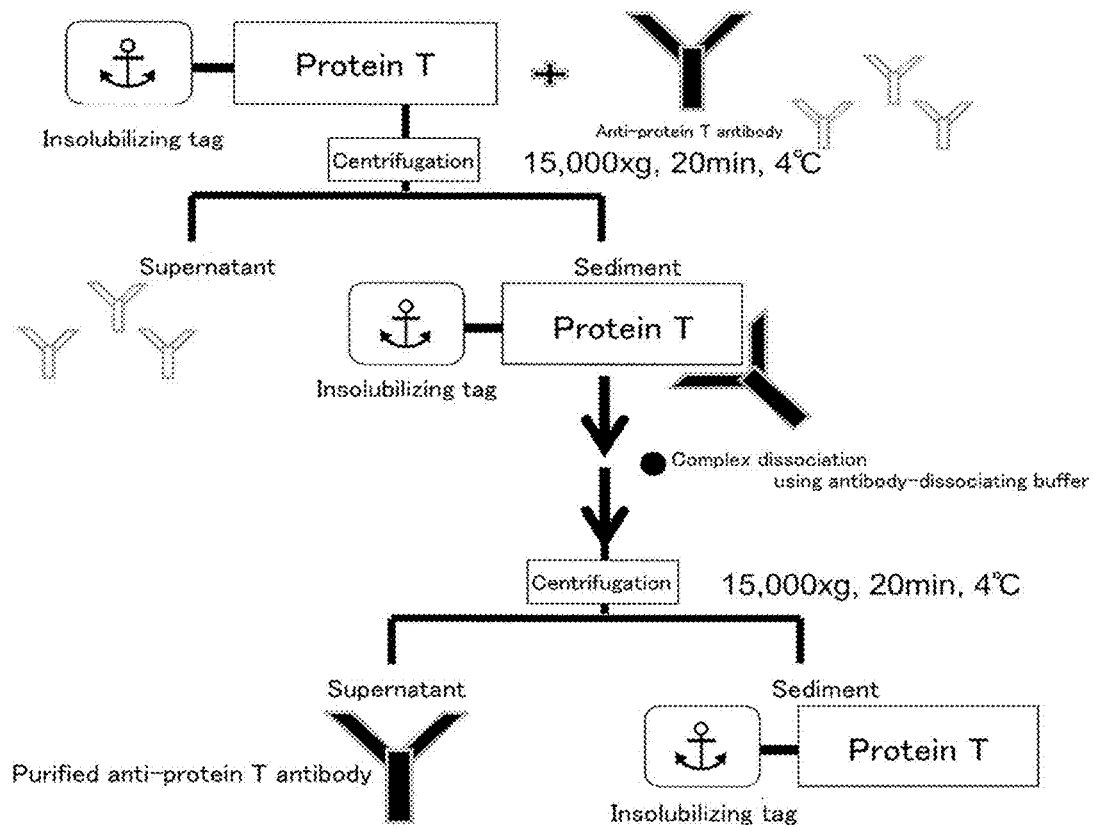
FIG. 7 is a view illustrating an example of the procedure of the antibody purification method according to the invention.

Referring to FIG. 7, the procedure of the antibody purification is described. First, an antibody fluid containing an antibody to be purified (anti-protein T antibody) and a tagged protein T are mixed and centrifuged (for example, 15,000×g, 20 minutes, 4° C.). After centrifugation, the anti-protein T antibody is separated as a complex with the tagged protein T binding it into the sediment. Subsequently, an antibody dissociation buffer is employed to dissociate the anti-protein T antibody from the complex, and centrifugation is conducted again. As a result of this centrifugation, the tagged protein T turns into the sediment and migrates into the insoluble fraction, thereby enabling the recovery of the anti-protein T antibody in the supernatant.

The tagged protein according to the present invention allows all proteins to be synthesized and purified regardless of the % solubilizability of the protein and the % retained affinity of the fusion protein, thus allowing the purification of all anti-protein antibodies to be accomplished. While the separation of the protein-antibody complex by centrifugation was exemplified here, the complex can be separated also by a trap using a filter and the like. By treating the complex trapped on the filter with the antibody dissociation buffer, the anti-protein antibody dissociated from the complex can be solubilized and recovered.

EXAMPLES

Example 1

1. Purification of Signal Transmission Protein Using Insolubilizing Tag (Wheat Cell-Free Expression System)

In this Example, a wheat cell-free expression system was employed to conduct synthesis and purification of a fusion protein between an insolubilizing tag according to the present invention and a signal transmission protein.

Using an entry clone in which the open reading frame (ORF) sequence of the signal transmission protein was cloned and a destination vector for fusion with the insolubilizing tag for the wheat cell-free expression system shown in FIG. 4, the protein synthesis using a wheat germ extract (WEPRO7240, CellFree Sciences Co., Ltd.) according to the method described in Non-patent Document 1. The gene symbol, the accession number of public database (GenBank: http://www.ncbi.nlm.nih.gov/genbank/), and the number of the entry clone (ID) of each signal transmission protein are shown in Table 1 to Table 3.

The solution after synthesis (crude protein solution) was subjected to a 4-fold dilution with PBS in order to reduce migration of the contaminant proteins upon purification, and centrifuged at 15,000×g and 4° C. for 20 minutes. The supernatant was removed and the sediment obtained (insoluble fraction) was designated as a purified protein fraction.

For comparison, using a destination vector for GST tag fusion, the protein synthesis was conducted similarly. The solution after the synthesis was subjected to 4-fold dilution with PBS, allowed to adsorb onto a glutathione resin (GE Pharmacia), and eluted with 0.8M glutathione, thereby recovering the purified protein.

TABLE 1

| Gene symbol | GenBank No. | Entry clone ID |
| --- | --- | --- |
| STAT1 | NM_139266.1 | FLJ39367AAAN |
| ATF4 | AK057751 | FLJ25022AAAN |
| PTK2 | AK094999 | FLJ37680AAAN |
| PTPN7 | AK127214 | FLJ45281AAAN |
| GBL | AK098762 | FLJ25896AAAN |
| RHEB | AK125446 | FLJ43457AAAN |
| TSC1 | NM_000368.3 | FLJ50429AAAN |
| PDK1 | NM_002610.3 | FLJ80165AAAN |
| MAPK14 | NM_139012.1 | FLJ80122AAAN |
| PRKCB | NM_002738.5 | FLJ80152AAAN |
| MAP2K2 | NM_030662.2 | FLJ80101AAAN |
| PRKCG | NM_002739.3 | FLJ92607AAAN |
| RAP1A | NM_001010935.1 | FLJ08033AAAN |
| PRKCA | NM_002737.2 | FLJ08071AAAN |
| SHC1 | BX647149.1 | FLJ08067AAAN |
| RAF1 | NM_002880.2 | FLJ92543AAAN |
| MAP2K4 | NM_003010.2 | FLJ93529AAAN |

TABLE 2

| Gene symbol | GenBank No. | Entry clone ID |
|---|---|---|
| ATF2 | AK128731 | FLJ46899AAAN |
| AKT1 | NM_005163.2 | FLJ08041AAAN |
| PRKCH | NM_006255.3 | FLJ08174AAAN |
| PRKCZ | NM_002744.4 | FLJ80058AAAN |
| HRAS | NM_005343.2 | FLJ82516AAAN |
| HRAS | NM_005343.2 | FLJ82516SAAN |
| AKT2 | NM_001626.2 | FLJ95460AAAN |
| ELK1 | NM_005229.2 | FLJ93445AAAN |
| MAPK3 | NM_002746.1 | FLJ80081AAAN |
| MAP2K1 | NM_002755.2 | FLJ76051AAAN |
| JUN | NM_002228.3 | FLJ82448WAAN |
| MYC | NM_002467.3 | FLJ85585SAAN |
| SOS1 | NM_005633.2 | FLJ76778AAAN |
| PRKCD | NM_006254.3 | FLJ93717AAAN |
| PRKCE | NM_005400.2 | FLJ94469AAAN |
| EGFR | NM_005228.3 | FLJ76780AAAN |
| KIAA1303 | NM_020761.1 | FLJ04039AAAN |

TABLE 3

| Gene symbol | GenBank No. | Entry clone ID |
|---|---|---|
| PRKAB1 | NM_006253.4 | FLJ92856AAAF |
| MAPKSP1 | NM_021970.2 | FLJ92015AAAF |
| NCK1 | NM_006153.3 | FLJ93089AAAF |
| RPS6KB1 | NM_003161.2 | FLJ93319AAAF |
| SRF | NM_003131.2 | FLJ51683AAAF |
| EIF4EBP1 | NM_004095.2 | FLJ92286AAAF |
| PRKCZ | NM_002744.4 | FLJ53316AAAF |
| STAT5A | NM_003152.2 | FLJ54464AAAF |
| MKNK2 | NM_017572.2 | FLJ54773AAAF |
| GAB1 | NM_002039.2 | FLJ53999AAAF |
| GRB2 | NM_002086.3 | FLJ96637AAAF |
| CRK | NM_016823.2 | FLJ81679AAAF |
| STAT5B | NM_012448.3 | FLJ82377AAAF |
| MAPK1 | NM_002745.4 | FLJ58314AAAF |
| FOS | NM_005252.2 | FLJ84847AAAF |
| STAT1 | NM_007315.2 | FLJ95929AAAF |
| PRKCI | NM_002740.4 | FLJ08175AAAF |

Figure 8:
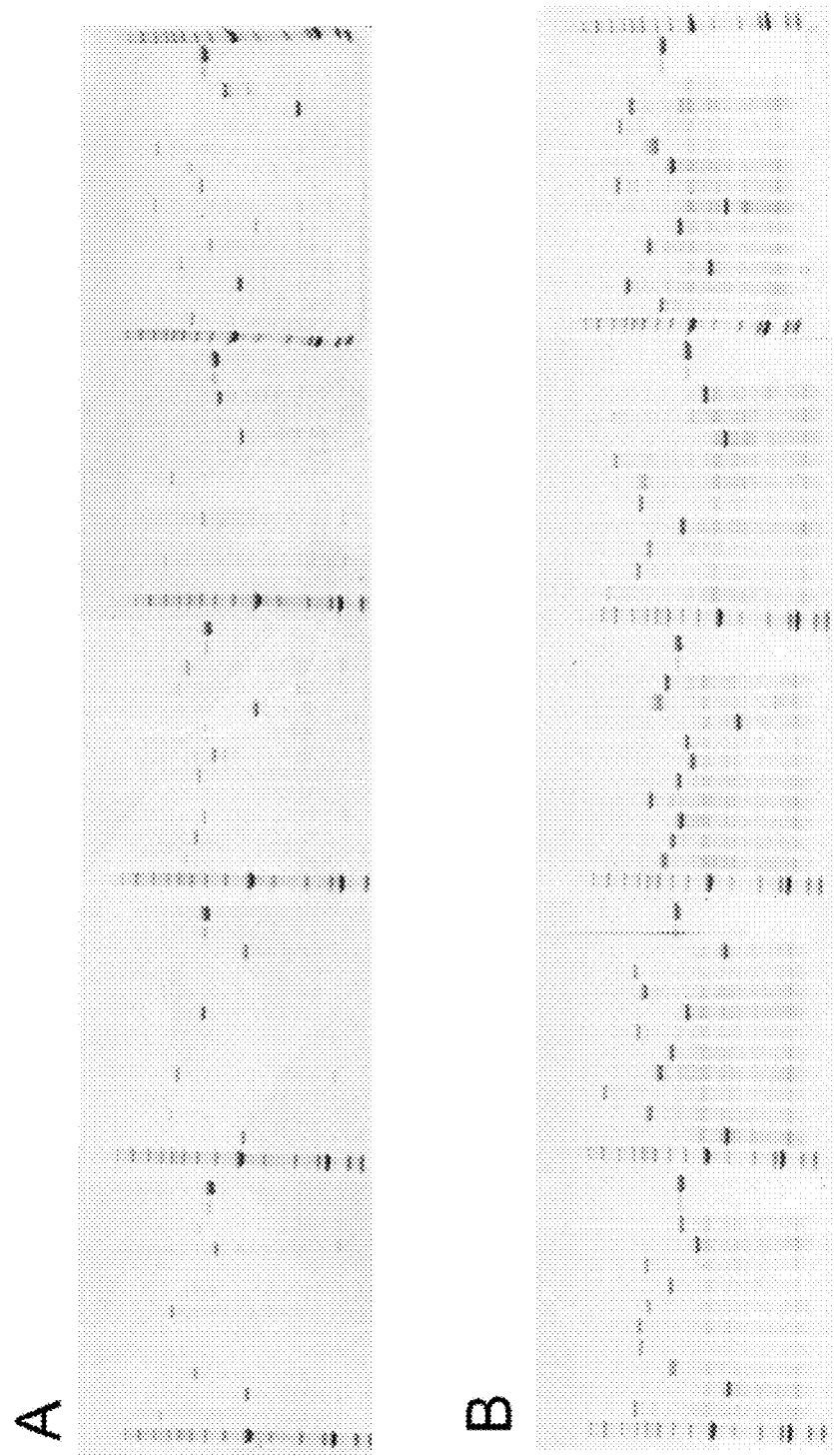
FIG. 8 is a drawing-substituting photograph showing the results of the purification of a signal transmission protein using an insolubilizing tag (Example 1).

The results are shown in FIG. 8. FIG. 8A shows the results of SDS-PAGE of the protein purified using GST tag. FIG. 8B shows the results of SDS-PAGE of the protein purified using the insolubilizing tag. FIG. 8B exhibited, unlike FIG. 8A, all protein bands with each protein band being exhibited more intensely when compared with that in FIG. 8A. Based on these results, it was clarified that by using the insolubilizing tag, the protein can be purified at a higher efficiency and a higher yield when compared with the purification method of the prior art employing GST tag.

Example 2

2. Purification of Fluorescent Protein or Enzyme Using Insolubilizing Tag

In this Example, a fusion protein between an insolubilizing tag according to the present invention and a fluorescent protein or enzyme was purified, and the purified fusion protein was verified whether it retained the fluorescence or the enzymatic activity.

Figure 9:
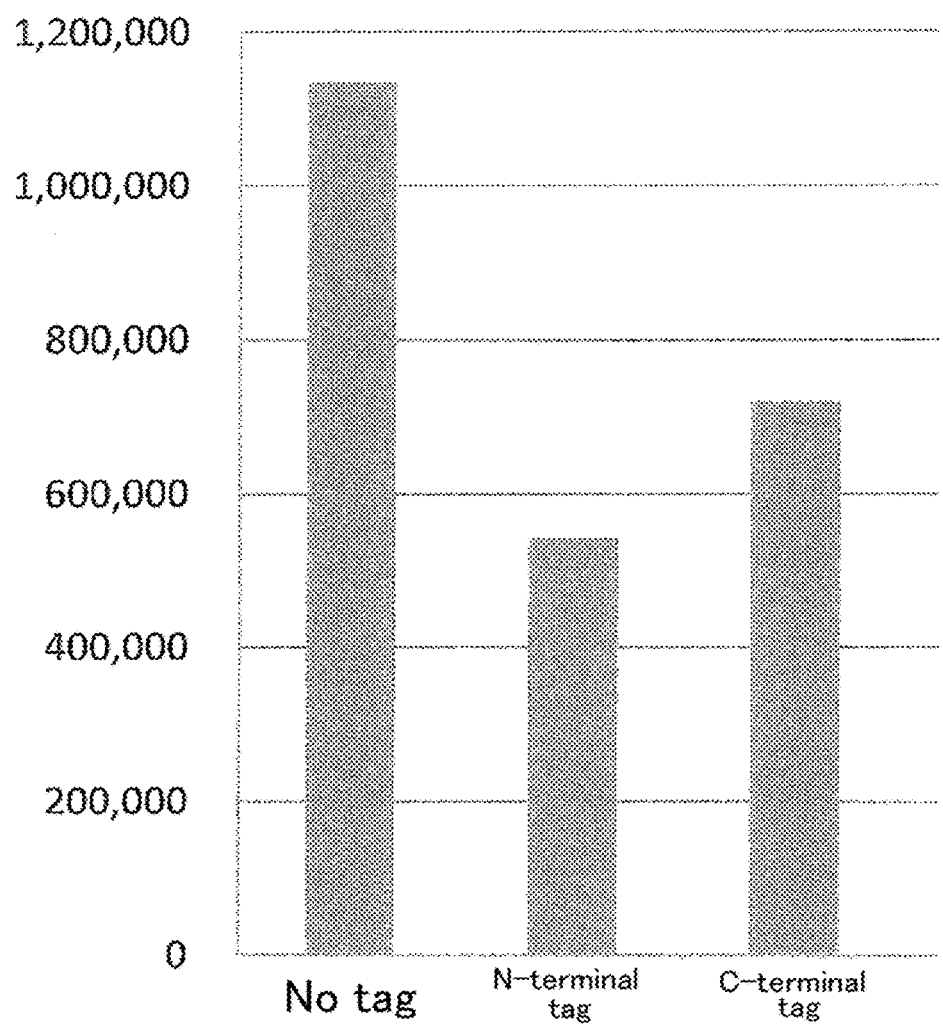
FIG. 9 is a drawing-substituting graph showing the results of the evaluation of the fluorescence of the fusion protein between the insolubilizing tag and a fluorescent protein (Example 2).

Similarly to Example 1, a fusion protein between a fluorescent protein and the insolubilizing tag was synthesized. The fluorescent protein employed was mVenus (Venus A206K, GenBank accession No. DQ092360.1). The results of measurement of the fluorescence of the crude protein solution (excitation wavelength 515 nm, fluorescent wavelength 528 nm) are shown in FIG. 9.

Even the fluorescent protein fused with the insolubilizing tag (N-terminal tag) exhibited a fluorescence at an intensity which was about a half of that of a non-tagged fluorescent protein. Also the fluorescent protein fused at the C-terminal with the insolubilizing tag exhibited a fluorescence.

Also similarly to Example 1, a fusion proteins between dephosphorylase or phosphorylases with an insolubilizing tag was synthesized. The dephosphorylases employed were DUSP3, PTPN1, and PTPN6. The phosphorylases employed were tyrosine kinases WEE1 and Hck1. The accession number of the public database of each enzyme is shown in Table 4.

TABLE 4

| Gene symbol | GenBank No. |
|---|---|
| DUSP3 | AK129822 |
| PTPN1 | NM_002827 |
| PTPN6 | NM_002831.3 |
| WEE1 | NM_003390.2 |
| Hck1 | NM_002827 |

The following method was employed to measure the phosphatase activity. Similarly to Example 1, a crude protein solution was centrifuged to obtain a purified protein fraction. The purified protein fraction was subjected to re-suspension with a buffer solution (50 mM Tris-HCl, pH7.5) and centrifugation each two times to remove contaminant proteins thereby obtaining a higher purity. The pellet after the centrifugation was combined with 3.0 µl of a buffer solution (50 mM Tris-HCl, pH7.5) and treated ultrasonically to obtain a suspension. The suspension and a pNpp chromogenic substrate were employed according to a standard method to measure the phosphatase activity by absorption photometry.

Figure 10:
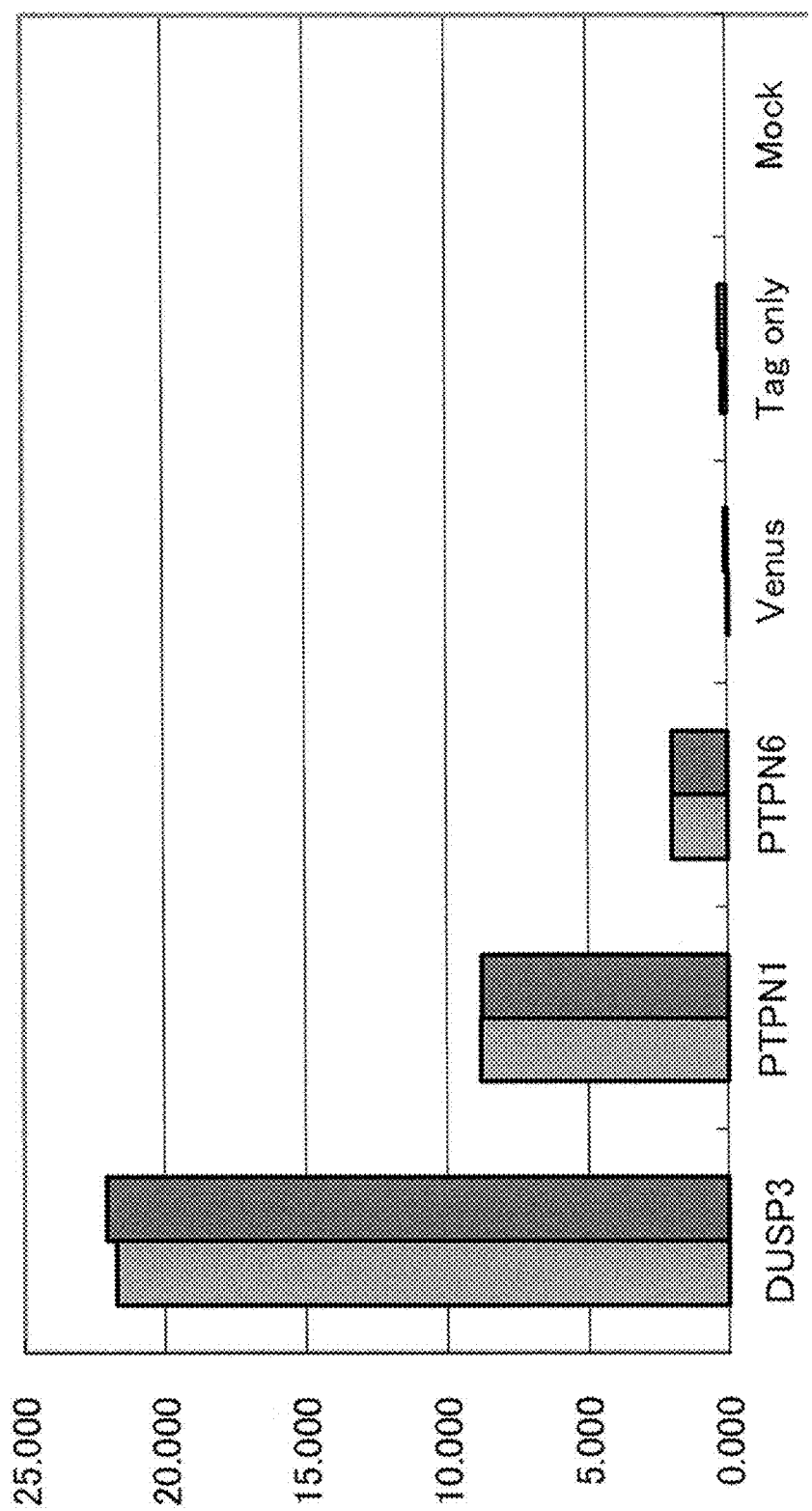
FIG. 10 is a drawing-substituting graph showing the results of the evaluation of the enzymatic activity of the fusion protein between the insolubilizing tag and a dephosphorylase (Example 2).

The results are shown in FIG. 10. Each of DUSP3, PTPN1, and PTPN6 had the enzymatic activity of the supernatant fraction obtained by centrifugation of the crude protein solution shown in the left bar of the graph and the enzymatic activity of the insoluble fraction (purified protein fraction) shown in the right bar of the graph. Every enzyme was proven to allow the activity of the fusion protein with the insolubilizing tag to be retained.

The following method was employed to measure the tyrosine kinase activity. Similarly to Example 1, the crude protein solution was centrifuged to obtain a purified protein fraction, which was dissolved in an LDS sample buffer (Life Technologies) and then subjected to the electrophoresis using NuPAGE electrophoresis system (Life Technologies) and Western blotting thereby evaluating the autophosphorylation ability of tyrosine kinase. The primary antibody employed was P-Tyr-100 antibody (mouse IgG, Cell Signaling Technology, Inc.), secondary antibody employed was anti-mouse IgG antibody (ovine IgG, HRP label, GE Healthcare), and detection was conducted using ECL-PLUS chemiluminescence detection kit (GE Healthcare).

Figure 11:
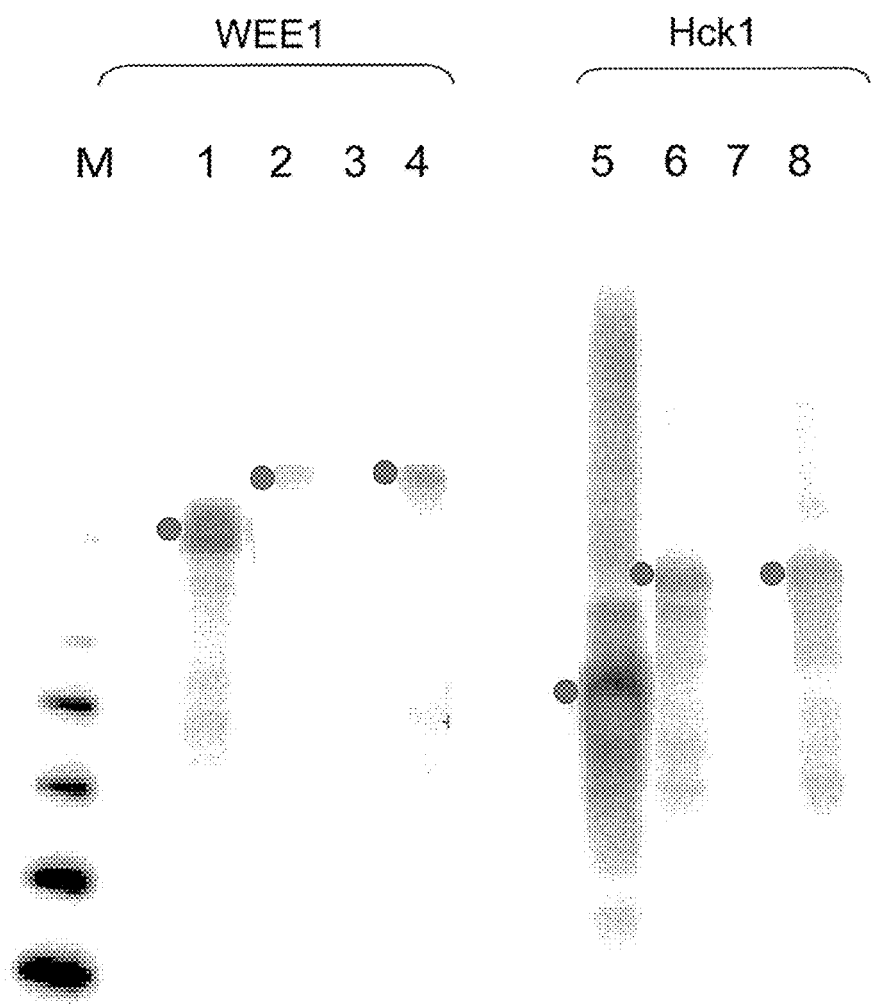
FIG. 11 is a drawing-substituting graph showing the results of the evaluation of the enzymatic activity of the fusion protein between the insolubilizing tag and a phosphorylase (Example 2).

The results are shown in FIG. 11. Lane 1 represents non-tagged WEE1 crude protein fraction, Lane 2 represents insolubilizing tag-fused WEE1 crude protein solution, Lane 3 represents insolubilizing tag-fused WEE1 centrifugation supernatant fraction, and Lane 4 represents insolubilizing tag-fused WEE1 centrifugation sediment purified protein fraction. Lane 5 represents non-tagged Hck1 crude protein fraction, Lane 6 represents insolubilizing tag-fused Hck1 crude protein solution, Lane 7 represents insolubilizing tag-fused Hck1 centrifugation supernatant fraction, Lane 8 represents insolubilizing tag-fused Hck1 centrifugation sediment purified protein fraction. Lanes 4 and 8 exhibited the bands binding to anti-phosphorylated tyrosine antibody (P-Tyr-100 antibody) (see circle symbol in Figure), and every enzyme was proven to allow the autophosphorylation ability of the fusion protein with the insolubilizing tag to be retained.

Based on the results of this Example, it was proven that tagging of a protein with the insolubilizing tag had no effect on the fluorescence and the enzymatic activity of the protein.

Example 3

3. Global Protein Purification Using Insolubilizing Tag

In this Example, an insolubilizing tag according to the present invention was used to conduct global protein purification.

Similarly to Example 1, 1026 types of the metabolism-associating proteins registered in KEGG (Kyoto Encyclopedia of Genes and Genomes, http://www.genome.jp/kegg/kegg_ja.html) were converted to fusion proteins with the insolubilizing tags, which were recovered by centrifugal fractionation into sediment fractions, whereby accomplishing purification.

Figure 12:
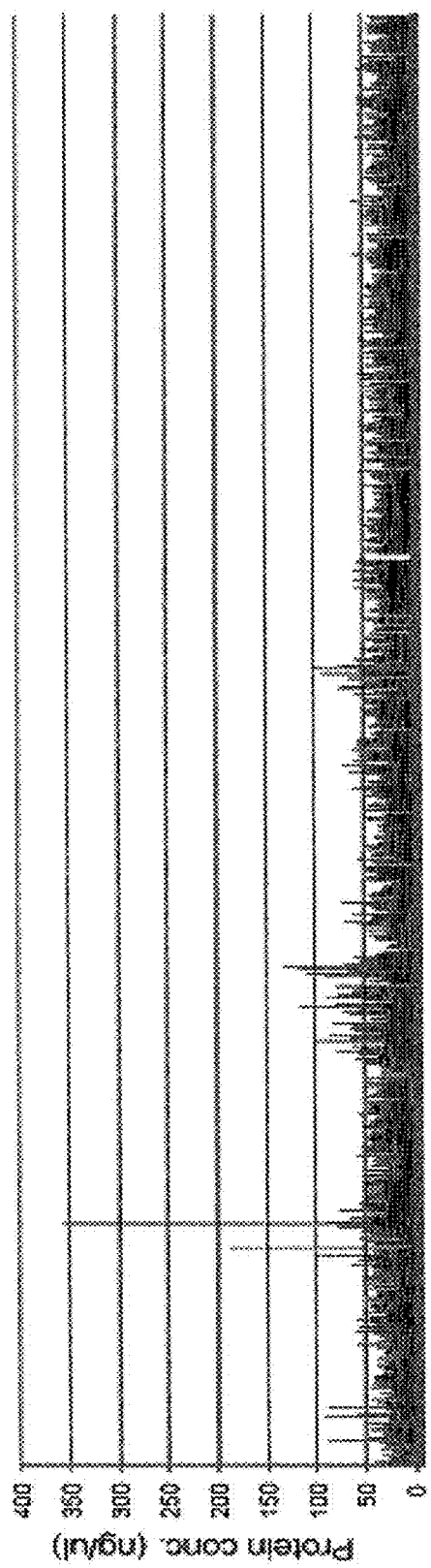
FIG. 12 is a drawing-substituting graph showing the results of the global protein purification using the insolubilizing tag (Example 3).

The purified proteins were quantified by electrophoresis using protein fluorescent prelabel method, and the results of which are shown in FIG. 12. The protein fluorescent prelabel method was conducted by introducing a fluorescent dye Cy5 into a lysine residue via amine coupling.

Example 4

4. Protein Array Production

In this Example, the protein purified using the insolubilizing tag according to the present invention was bound to a substrate to produce a protein array.

Similarly to Example 1, an entry clone into which the ORF sequence of the protein shown in Table 5 was cloned was used to synthesize a fusion protein between the protein (see Table 5) and an insolubilizing tag, which was centrifuged to obtain the sediment (insoluble fraction) as a purified protein fraction. The purified protein fraction was suspended in a dissolution solution (0.04% SDS (w/v) and 0.1M phosphate buffer (pH7.8)), and mixed with shaking for about 1 minutes, and then treated ultrasonically three times each for 1 minute (high frequency output with 160 W, 40 kHz) thereby obtaining a solubilized solution of the purified protein having the insolubilizing tag attached thereto.

TABLE 5

| Gene symbol | GenBank No. | Entry clone ID |
|---|---|---|
| TRIM21 | NM_003141.3 | FLJ81065AAAF |
| MGLL | NM_007283.6 | FLJ96595AAAF |
| CT45A5 | NM_001172288.1 | FLJ83136AAAF |

As substrates of the protein array of this Example, two types of the substrates, namely, SuperNHS produced by Arrayit and FAST Slide 1-Pad produced by GE Healthcare were employed. The solubilized solution containing each fusion protein was spotted onto each substrate using a micro dispenser or a pin tool, and the protocol by the supplier of each substrate was followed to effect the binding reaction between the fusion protein and the surface of the substrate. Also for obtaining a negative control or a positive control in Example 5 described below, fluorescent protein Venus and purified human IgG were also attached to the aforementioned substrate.

On the substrate, the solubilized solution containing the attached protein was dried, and then TBST (20 mM Tris-HCl (pH8.0), 134 mM NaCl, 0.1% (v/v) Tween20) was used to wash the surface of the substrate to remove the protein which had not bound to the surface of the substrate, thereby establishing the protein array.

Example 5

5. Detection of Autoantibody by Protein Array

The protein array produced in Example 4 was used to detect serum autoantibody.

A human serum containing anti-TRIM21 antibody and anti-CT45A5 antibody as autoantibodies was employed. This human serum was subjected to 1000-fold dilution with TBST containing 3% (w/v) skimmed milk to obtain a primary antibody solution. The protein array produced in Example 4 was immersed preliminarily in 3% (w/v) skimmed milk-containing TBST at room temperature for 1 hour, thereby blocking the surface of the substrate. After blocking, the surface of the substrate was immersed in the primary antibody solution, and allowed to stand at room temperature for 1 hour while agitating the primary antibody solution. Thereafter, TBST was used to wash the surface of the substrate.

In order to detect autoantibody contained in the primary antibody solution, fluorescent dye Alexa647-labeled anti-human IgG antibody was employed as a secondary antibody, and this anti-human IgG antibody was subjected to 1000-fold dilution with 3% (w/v) skimmed milk-containing TBST to obtain a secondary antibody solution. The surface of the substrate was immersed in the secondary antibody solution, and allowed to stand at room temperature for 1 hour while agitating the secondary antibody solution. Thereafter, TBST was used to wash the surface of the substrate. After treatment with the secondary antibody, a fluorescent scanner was used with an excitation wavelength of 635 nm to measure the fluorescence emitted from the surface of each substrate at a PMT of 420 V for SuperNHS protein array and at a PMT of 200 V for FAST Slide substrate.

Figure 14:
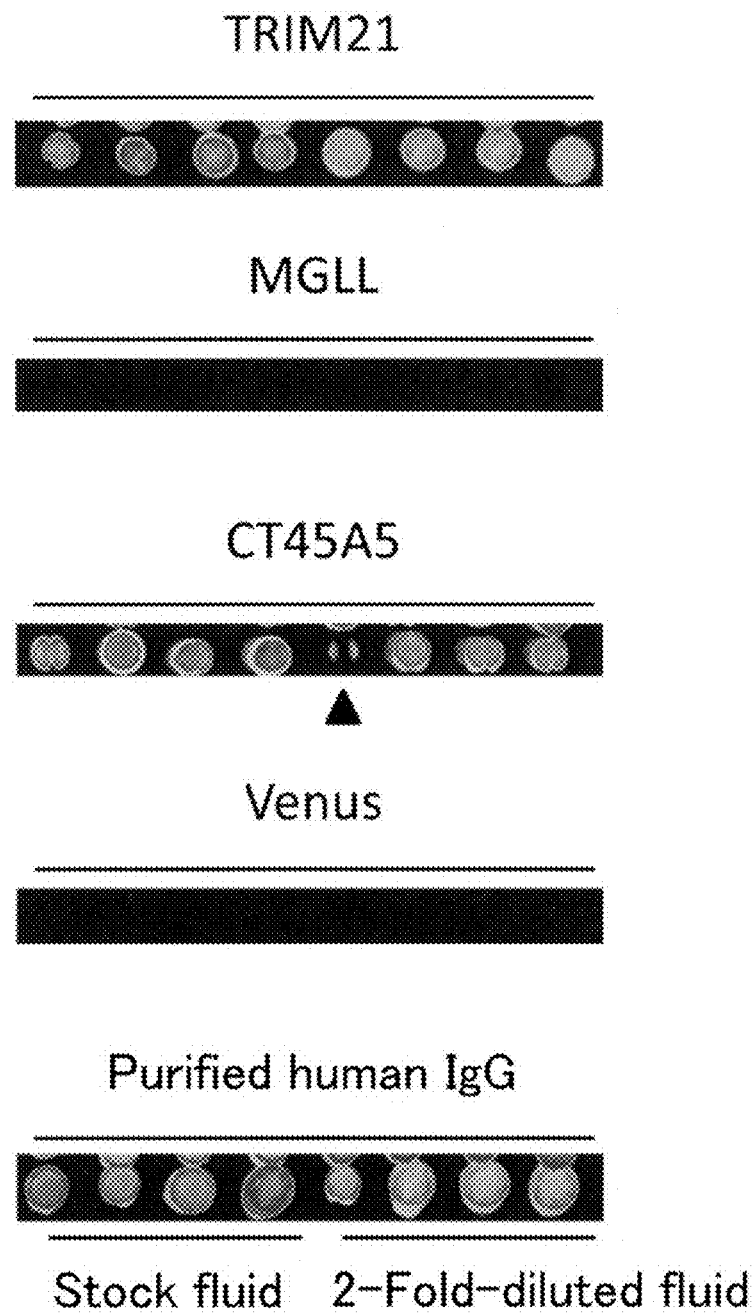
FIG. 14 is a drawing-substituting photograph showing the results of the detection of the autoantibody using the protein array made in Example 4 (Example 5).
Figure 15:
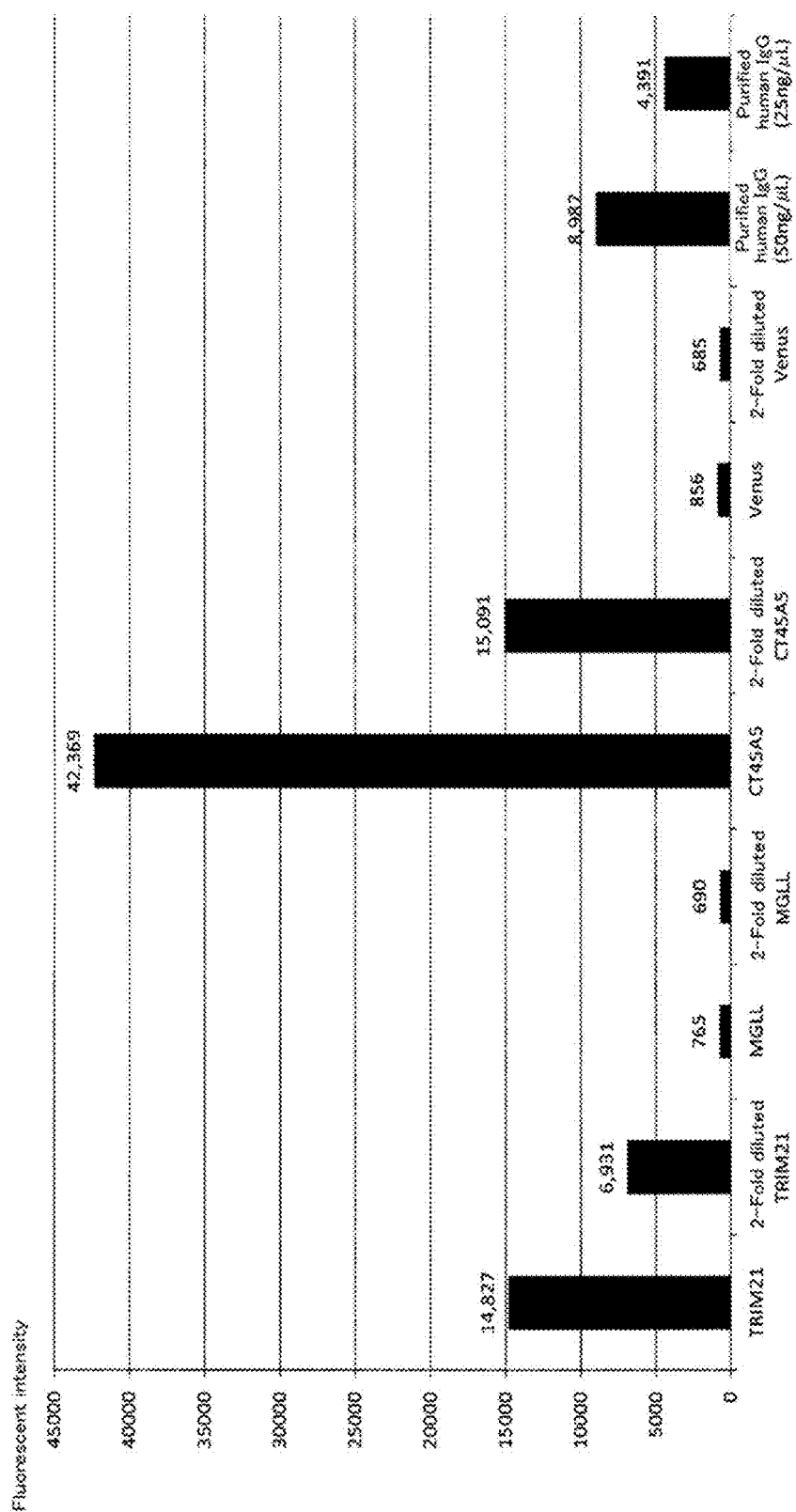
FIG. 15 is a drawing-substituting graph showing the results of the detection of the autoantibody using the protein array made in Example 4 (Example 5).
Figure 16:
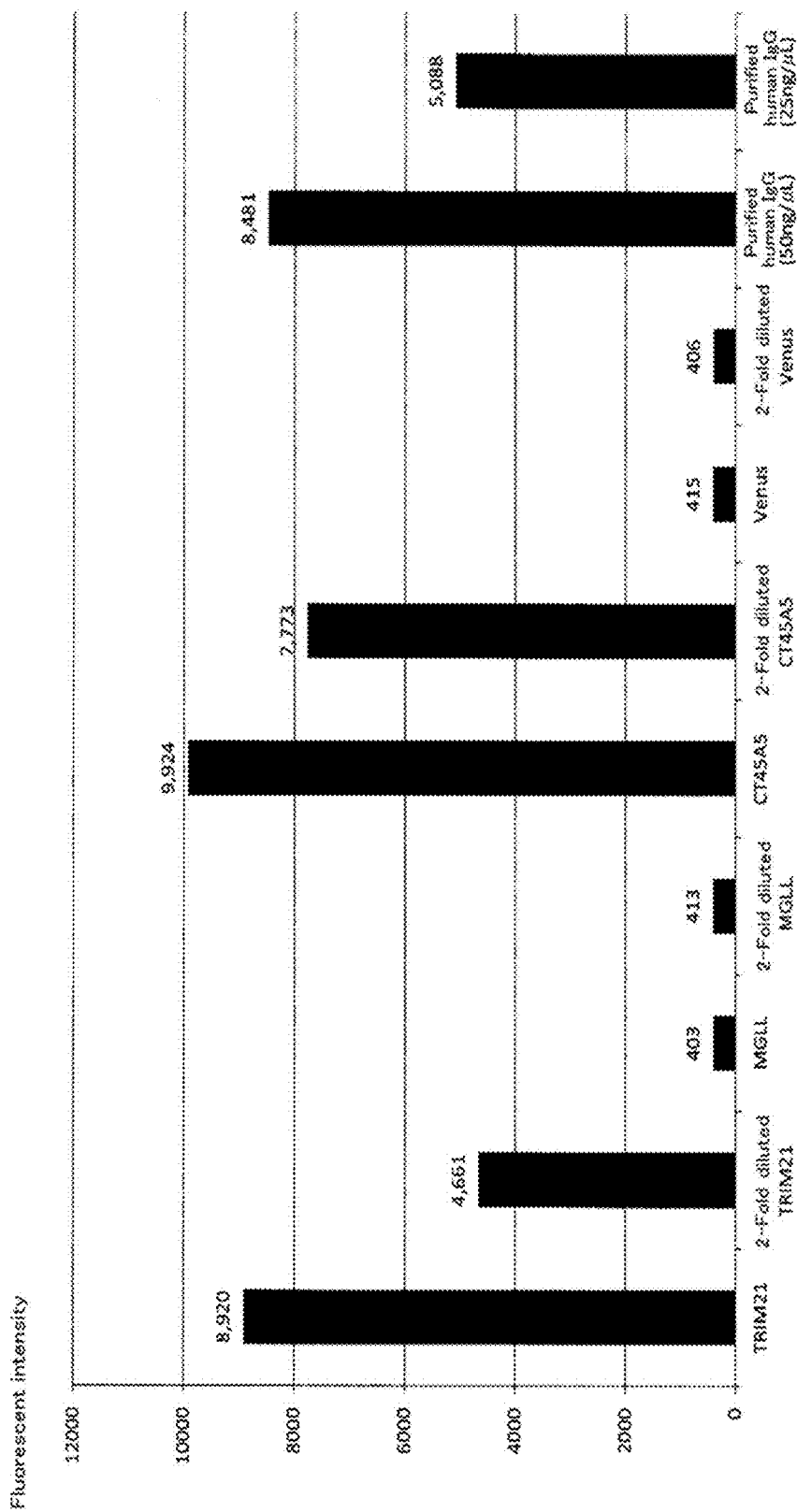
FIG. 16 is a drawing-substituting graph showing the results of the detection of the autoantibody using the protein array made in Example 4 (Example 5).

The results of this Example are shown in FIG. 13 to FIG. 16. FIG. 13 and FIG. 14 show the results of the measurement of the fluorescence emitted from the spots of each protein on the substrate. FIG. 13 shows the results when the substrate employed was SuperNHS, while FIG. 14 shows the results when the substrate employed was FAST Slide 1-Pad. FIG. 15 is a graph of the numerical value of the fluorescent intensity of each spot shown in FIG. 13, while FIG. 16 is a graph of the numerical value of the fluorescent intensity of each spot shown in FIG. 14. The spot arrowed in FIG. 14 was excluded from the fluorescence measurement because of insufficient binding of the protein to the substrate.

As shown in FIG. 13 to FIG. 16, the spots of TRIM21 and CT45A5 having autoantibodies in serum allowed the fluorescence derived from the secondary antibody to be measured. The intensity of the measured fluorescence was in proportion with the quantity of the protein attached to the substrate. This means that the primary antibody had bound specifically to the protein attached to the substrate. On the other hand, the spot of MGLL which was a protein having no antibody in serum exhibited a measured fluorescence whose intensity was lower than the fluorescent intensity measured from the spot of the aforementioned TRIM21 or CT45A5. The spot of the purified human IgG as a positive control exhibited a measured fluorescent intensity comparable with that of TRIM21. On the other hand, the spot of Venus as a negative control exhibited a measured fluorescent intensity comparable with that of the spot of the aforementioned MGLL.

Based on the results of this Example, the protein purified using the insolubilizing tag according to the present invention was confirmed, in the analysis using the protein array, to have been purified to a level suitable for specific detection with an antibody. Accordingly, the protein purified using the insolubilizing tag according to the present invention can be used for a protein array by being bound onto a substrate.

Example 6

6. Purification of Protein Using Insolubilizing Tag (*E. coli* Intracellular Expression System)

In this Example, *E. coli* intracellular expression system was employed to purify a fusion protein between an insolubilizing tag according to the present invention and GST.

Figure 17:
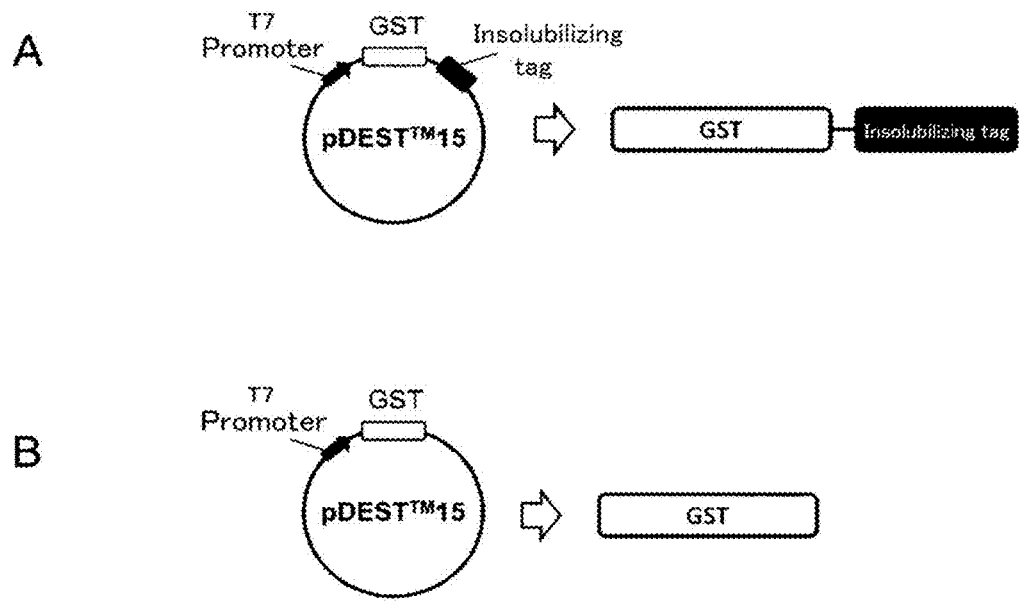
FIG. 17 is a view illustrating a vector employed in an *E. coli* cell expression system (Example 6).

In this Example, a vector for expression in *E. coli* (pD-EST15) shown in FIG. 17 was employed. FIG. 17A is a vector for synthesizing GST to which the insolubilizing tag was attached. On the other hand, FIG. 17B is a vector for synthesizing only GST. Each vectors shown in FIG. 17A and FIG. 17B was introduced into *E. coli* to obtain a transformed *E. coli*. The transformed *E. coli* was cultured overnight at 37° C., and the resultant *E. coli* culture fluid was diluted to an $OD_{600}$ of 0.5, and the diluted fluid thus obtained was supplemented with L-arabinose at a concentration of 0.1%, thereby starting the induction of expression. Immediately after inducing the expression (time 0) and 3 hours after inducing the expression, the diluted fluid was each recovered and centrifuged to obtain the cells.

The resultant cells were supplemented with 100 μl of PBS, suspended again, and treated ultrasonically 20 times each for 1 minute (high frequency output 160 W, 40 kHz). After the ultrasonic treatment, the suspension containing the cells was partly subjected as it was to SDS-PAGE. The suspension was also centrifuged at 19000×g for 20 minutes at 4° C. to obtain the supernatant and the sediment. These supernatant and sediment were also employed in SDS-PAGE.

Figure 18:
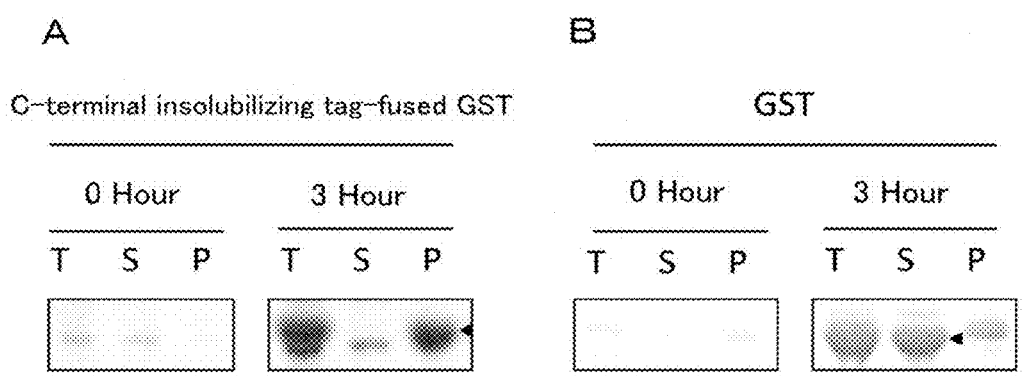
FIG. 18 is a drawing-substituting photograph showing the results of the purification of a protein using the insolubilizing tag (Example 6).

The results of this Example are shown in FIG. 18. Three hours after expression, the suspension obtained from *E. coli* to which the vector shown in FIG. 17A had been introduced exhibited a band at the position corresponding to the molecular weight judged to be of GST whose C terminal had the insolubilizing tag attached thereto (see FIG. 18A, T). On the other hand, the suspension obtained from *E. coli* to which the vector shown in FIG. 17B had been introduced exhibited a band at the position corresponding to the molecular weight judged to be of GST (see FIG. 18B, T).

From the supernatant and the sediment obtained by centrifuging the suspension, GST whose C terminal had the insolubilizing tag attached thereto was observed almost exclusively in the sediment (see FIG. 18A, arrowhead). On the other hand, GST was observed almost exclusively in the supernatant (see FIG. 18B, arrowhead).

Based on the results of this Example, the insolubilizing tag according to the present invention was proven to allow, even when the protein was synthesized using an *E. coli* cell expression system, the fusion protein having the insolubilizing tag attached thereto to be insolubilized.

Test Example 1

7. Insolubilizing Tag Domainization

In this Test Example, among the full-length amino acids of MafG protein, the partial sequence (domain) specifically contributing the insolubility was identified.

Figure 19:
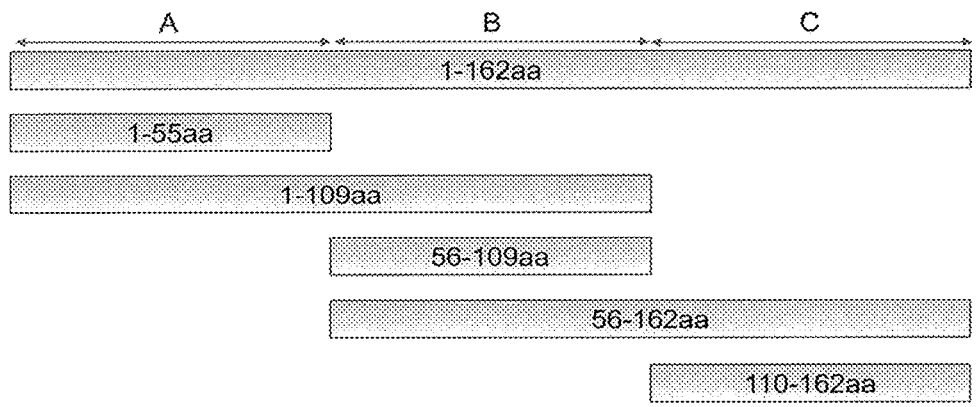
FIG. 19 is a view illustrating the domain of the insolubilizing tag (Test Example 1).

The full-length amino acids of MafG protein were divided into 3 domains to obtain domain A consisting of 1st to 55th amino acids from the N-terminal, domain B consisting of 56th to 109th amino acids from the N-terminal, and domain C consisting of 110th to 162nd amino acids from the N-terminal (see FIG. 19). Vectors capable of expressing 5 types of insolubilizing tags consisting of the amino acid sequences of the full-length, only domain A, domain A and domain B, only domain B, domain B and domain C, and only domain C were constructed. At the N-terminal of each insolubilizing tag, methionine was attached. Into the ORFs of the vector, fluorescent protein mVenus or cDNA of a highly soluble protein GST was inserted. Using these vectors, fusion proteins were synthesized using a wheat cell-free system, and centrifuged and then subjected to SDS-PAGE.

Figure 20:
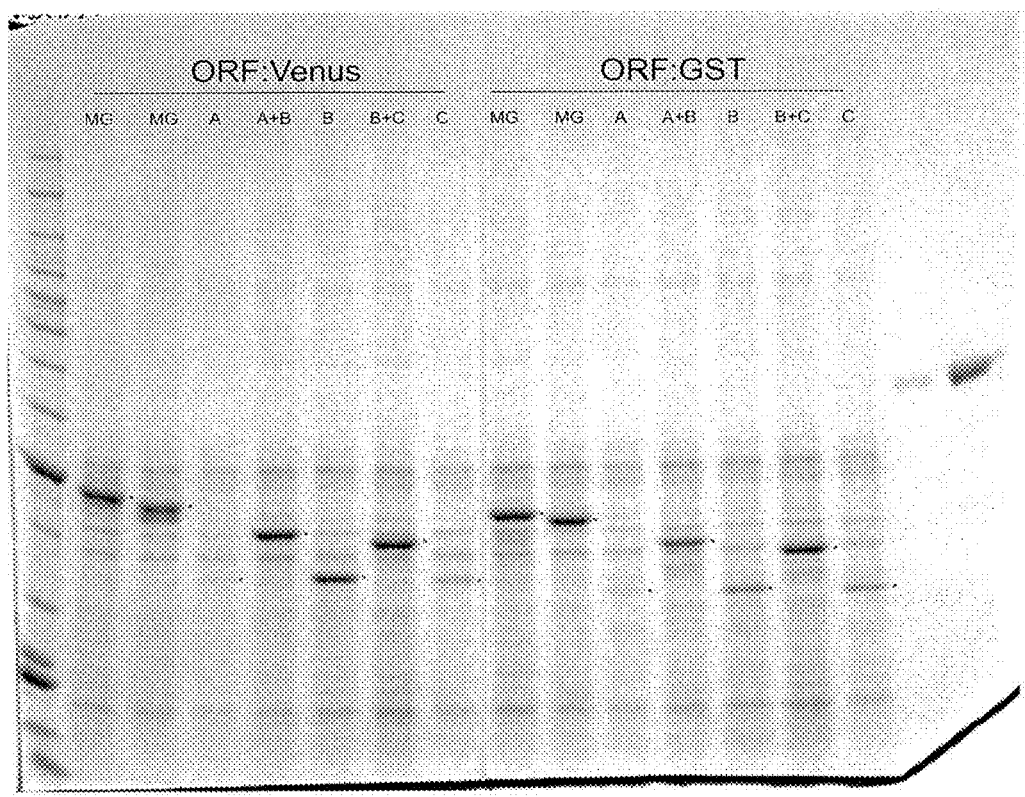
FIG. 20 is a drawing-substituting photograph showing the results of domainization of the insolubilizing tag (Test Example 1).

The results of the comparison of the recovery levels among 5 types of the insolubilizing tag are shown in FIG. 20. In any of the fusion protein with Venus and the fusion protein with GST, the insolubilizing tag consisting of the amino acid sequences of domain B and domain C (B+C) exhibited the recovery level comparable with that of the insolubilizing tag consisting of the full-length amino acid sequence (MG). On the other hand, the insolubilizing tags consisting of the amino acid sequences of only domain A (A), domain A and domain B (A+B), only domain B (B), and only domain C (C) exhibited reduced recovery levels when compared with that of the insolubilizing tag consisting of the full-length amino acid sequence (MG). Based on these results, it was found that, among the full-length amino acids of MafG protein, domain B and domain C especially contributes to the insolubility, and that the insolubilizing tag can be effective even when being reduced to the 107 residues of domain B and domain C.

Test Example 2

8. Insertion of Protease Cleavage Sites

In this Test Example, into the amino acid sequence of domain B and domain C obtained in Test Example 1, amino acids serving as protease cleavage sites were inserted to alter the amino acid sequence of the insolubilizing tag.

The insolubilizing tag consisting of the full-length amino acids of MafG protein (SEQ ID NO:1) was designated as Version 1, and the following insolubilizing tags were further produced, i.e., the amino acid sequence of domain B and domain C having 10 arginine residues inserted thereinto designated as Version 2 (SEQ ID NO:3) as well as Version 2 further having 7 arginine residues inserted thereinto designated as Version 3 (SEQ ID NO:4). For the typical amino acid sequence of each insolubilizing tag, see FIG. 3. The Version 2 insolubilizing tag had arginine residues added as being inserted thereinto so that the length of the tag-derived peptide after trypsin treatment became 6 residues or less. The Version 3 insolubilizing tag had more arginine residues added as being inserted thereinto.

Using vectors capable of expressing the fusion proteins between these insolubilizing tags and 12 types of the proteins (see Table 6), the proteins were synthesized using a wheat cell-free system, centrifuged and then subjected to SDS-PAGE, thereby comparing the recovery levels of the fusion proteins.

TABLE 6

| Lane | Gene symbol | Protein | GenBank or Ensembl No. | Entry clone ID |
|---|---|---|---|---|
| 1 | CCNB2 | cyclin B2 [Homo sapiens]. | AK001404 | FLJ10542AAAN |
| 2 | CCNL2 | cyclin L2 isoform A [Homo sapiens]. | ENST00000360054 | FLJ14864AAAN |
| 3 | CCND3 | cyclin D3 isoform 1 [Homo sapiens]. | AK057206 | FLJ32644AAAN |
| 4 | CCNJ | cyclin J isoform 3 [Homo sapiens]. | AK092360 | FLJ35041AAAN |
| 5 | CUL1 | cullin 1 [Homo sapiens]. | AK096163 | FLJ38844AAAN |
| 6 | CDC25C | cell division cycle 25C isoform a [Homo sapiens]. | AK097710 | FLJ40391AAAN |
| 7 | RAD21 | RAD21 homolog [Homo sapiens]. | AK098521 | FLJ25655AAAN |
| 8 | WEE1 | WEE1 tyrosine kinase isoform 2 [Homo sapiens]. | AK122837 | FLJ16446AAAN |
| 9 | CDK7 | cyclin-dependent kinase 7 [Homo sapiens]. | AK026509 | FLJ22856AAAN |
| 10 | SMC2 | structural maintenance of chromosomes 2 [Homo sapiens]. | AK001485 | FLJ10623AMN |
| 11 | CCNA1 | cyclin A1 isoform c [Homo sapiens]. | ENST00000255465 | FLJ50745AAAN |
| 12 | AURKA | serine/threonine protein kinase 6 [Homo sapiens]. | ENST00000312783 | FLJ80023AAAN |

Figure 21:
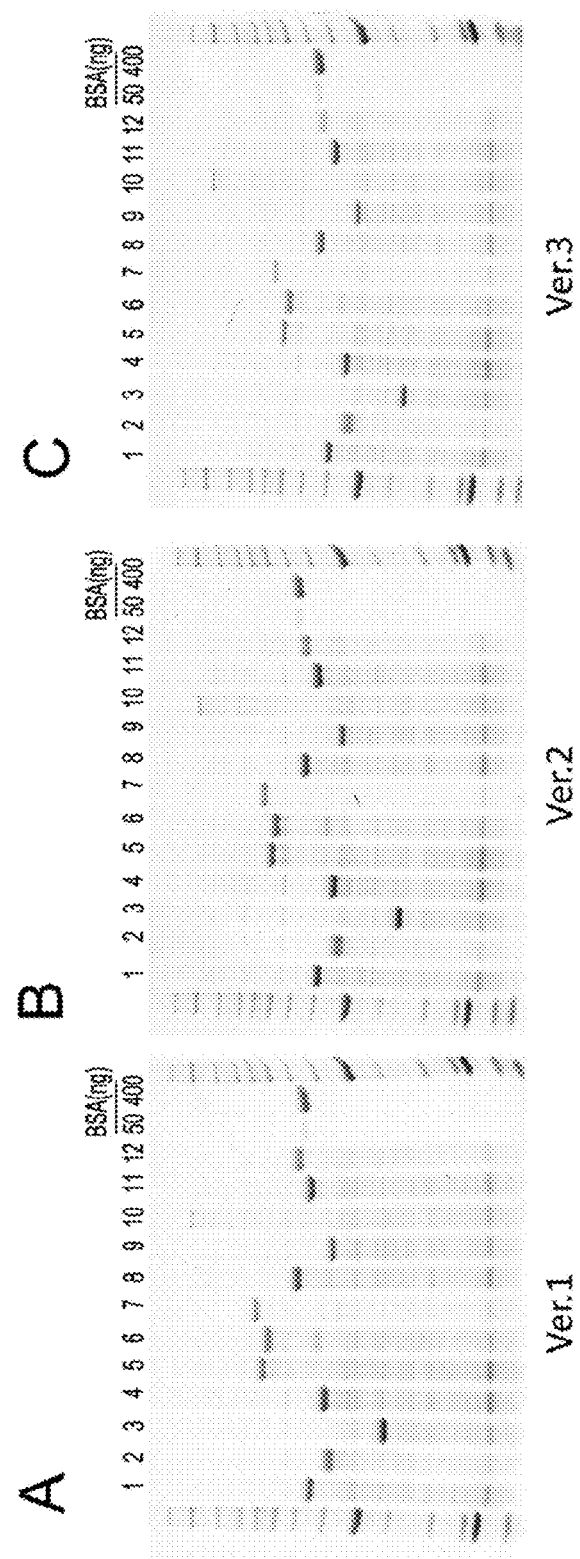
FIG. 21 is a drawing-substituting photograph showing the results of the purification of a protein using an insolubilizing tag into which a protease cleavage site was inserted (Test Example 2).

(The lane number in the table corresponds to the lane number in FIG. 21. For public database Ensembl, see http://asia.ensembl.org/index.html)

The results are shown in FIG. 21. The results of SDS-PAGE of the fusion proteins are shown in FIG. 21A for Version 1, FIG. 21B for Version 2, and FIG. 21C for Version 3. The Version 2 insolubilizing tag exhibited a % protein recovery comparable with that of the Version 1 insolubilizing tag. On the other hand, the Version 3 insolubilizing tag exhibited a somewhat reduced % protein recovery when compared with that of the Version 1 insolubilizing tag. Based on these results, it is suggested that when using the shortest amino acid sequence (107 residues) domainized in Test Example 1 as an amino acid sequence of the insolubilizing tag, the preferable number of the inserted amino acids serving as protease cleavage sites was less than 17. It is also suggested that, while a larger number of the amino acid insertions results in a shorter tag-derived peptide after protease treatment, a too large number reduces the insolubility of the insolubilizing tag and increases solubility of the fusion protein which may reduce the efficiency of recovery by centrifugation.

Test Example 3

9. Investigation of Tagged Protein Re-Solubilization Condition

For re-solubilization of a fusion protein having an insolubilizing tag attached thereto (tagged protein) which was recovered as an insolubilized fraction, suitable solvents were searched for.

Similarly to Example 1, a fusion protein between a fluorescent protein mVenus (Venus A206K, GenBank accession No. DQ092360.1) and an insolubilizing tag was synthesized using a wheat cell-free expression system. Also using an entry clone in which the ORF sequence of the immunoglobulin heavy chain gamma 3 constant region (IgHG3, GenBank accession No. AK097355) was cloned (entry clone ID FLJ40036AAAF), a fusion protein between IgHG3 and an insolubilizing tag was synthesized similarly using the wheat cell-free expression system.

The suspension containing the synthesized tagged protein was centrifuged under the condition of 19,000×g, 20 minutes, and 4° C. to recover the tagged protein as an insolubilized fraction. The resultant insolubilized fraction was combined with any one type of the solvents shown in Table 7, mixed with shaking for 1 minute, and treated ultrasonically three times each for 1 minute (high frequency output 160 W, 40 kHz). The suspension containing the tagged protein was centrifuged again at 19,000×g for 20 minutes at 4° C., and the supernatant was used as a dissolution solution for the tagged protein.

TABLE 7

| Solvent | Composition |
|---|---|
| 1 | Hydrochloric acid aqueous solution (pH 3.0) |
| 2 | Hydrochloric acid aqueous solution (pH 4.0) |
| 3 | Hydrochloric acid aqueous solution (pH 5.0) |
| 4 | Acetic acid aqueous solution (pH 3.0) |
| 5 | Acetic acid aqueous solution (pH 4.0) |
| 6 | Acetic acid aqueous solution (pH 5.0) |
| 7 | 10 µM Sodium hydroxide aqueous solution (pH 9.0) |
| 8 | 100 µM Sodium hydroxide aqueous solution (pH 10.0) |
| 9 | 1 µM Sodium hydroxide aqueous solution (pH 11.0) |
| 10 | 0.01M Sodium hydroxide aqueous solution (pH 12.0) |
| 11 | 0.1M L-arginine aqueous solution |
| 12 | 0.5M L-arginine aqueous solution |
| 13 | 1M L-arginine aqueous solution |
| 14 | 2M L-arginine aqueous solution |
| 15 | 50 mM Tris HCl buffer solution (pH 8.0) |
| 16 | 0.0016% SDS/50 mM Tris HCl buffer solution (pH 8.0) |
| 17 | 0.008% SDS/50 mM Tris HCl buffer solution (pH 8.0) |
| 18 | 0.04% SDS/50 mM Tris HCl buffer solution (pH 8.0) |
| 19 | 0.2% SDS/50 mM Tris HCl buffer solution (pH 8.0) |
| 20 | 1% SDS/50 mM Tris HCl buffer solution (pH 8.0) |
| 21 | 0.04% SDS/100 mM Phosphate buffer solution (pH 5.8) |
| 22 | 0.04% SDS/100 mM Phosphate buffer solution (pH 6.8) |
| 23 | 0.04% SDS/100 mM Phosphate buffer solution (pH 7.8) |
| 24 | 0.04% SDS/100 mM Sodium hydrogen carbonate buffer solution (pH 9.2) |

The dissolution solution of the tagged protein was subjected to SDS-PAGE, and the gel after running was stained with Coomassie brilliant blue (CBB), and the chromogenic intensity of the band attributable to the fusion protein was measured. Also using a BSA dissolution solution containing bovine serum albumin (BSA) at a certain concentration, a calibration curve indicating the chromogenic intensity of CBB versus the protein level was obtained. Based on this calibration curve, the level of the tagged protein contained in the dissolution solution of the tagged protein was calculated, and the proportion of the tagged protein solubilized again after being recovered into the insolubilized fraction was investigated.

The results of this Test Example are shown in Table 8. In the table, "-" indicates no investigation. As shown in Table 8, the fusion proteins between mVenus and the insolubilizing tag were hardly re-solubilized when using Solvents 2, 11, 12, and 15. The fusion protein between IgHG3 and the insolubilizing tag were hardly re-solubilized when using Solvents 1 and 4 to 8. On the other hand, when using Solvents 10, 18, and 23, both fusion proteins exhibited re-solubilization of almost entire amounts of the fusion proteins recovered into the insolubilized fractions.

TABLE 8

| Solvent | % Solubilizability | |
|---|---|---|
| | mVenus | IgHG3 |
| 1 | — | 0 |
| 2 | 0 | 20 |
| 3 | — | 20 |
| 4 | — | 0 |
| 5 | — | 0 |
| 6 | — | 0 |
| 7 | — | 0 |
| 8 | — | 0 |
| 9 | 20 | 30 |
| 10 | 99 | 99 |
| 11 | 0 | — |
| 12 | 0 | — |
| 13 | 50 | — |
| 14 | — | 99 |
| 15 | 0 | — |
| 16 | — | 10 |
| 17 | 10 | 30 |
| 18 | 99 | 99 |
| 19 | 99 | — |
| 20 | 99 | — |
| 21 | — | 70 |
| 22 | — | 80 |
| 23 | 99 | 99 |
| 24 | — | 99 |

As shown in the % solubilizabilities in Solvents 16 to 20, when using the solvent containing SDS at a concentration within the range of 0.04 to 1% (w/v), the fusion proteins between Venus and the insolubilizing tag recovered into the insolubilized fraction were re-solubilized almost entirely (Table 8). In addition, as shown in the % solubilizabilities in Solvents 21 to 24, the solvent containing SDS at a concentration of 0.04% (w/v) exhibited a high % solubilizability of the tagged protein at pI17.8 to pI19.2, and almost entire amount of the fusion protein between IgHG3 and the insolubilizing tag recovered into the insolubilized fraction was re-solubilized (Table 8).

Test Example 4

10. Re-Solubilization of Fusion Protein with Insolubilizing Tag by Solvent

Solvent 23 investigated in Test Example 3 (see Table 7) was further verified whether it was suitable for re-solubilization of fusion proteins with several other insolubilizing tags (tagged proteins).

Similarly to Example 1, an entry clone into which the ORF sequence of the protein shown in Table 9 was cloned was used to synthesize a fusion protein between the protein (see Table 9) and an insolubilizing tag, which was centrifuged to obtain the sediment (insoluble fraction) as a purified protein fraction. The purified protein fraction was combined with Solvent 23 similarly to Test Example 3 to obtain a dissolution solution of the tagged protein. The quantification of the tagged protein contained in the dissolution solution was conducted similarly to Test Example 3.

TABLE 9

| Gene symbol | GenBank No. | Entry clone ID |
|---|---|---|
| TRIM21 | NM_303141.3 | FLJ81065AAAF |
| MGLL | NM_007283.6 | FLJ96595AAAF |
| CT45A5 | NM_001172288.1 | FLJ83136AAAF |
| CD320 | NM_016579.3 | FLJ96747AAAF |
| RGS6 | NM_004296.5 | FLJ94029AAAF |
| IRX2 | NM_033267.4 | FLJ82376AAAF |
| TOP3A | AK126869 | FLJ77247AAAN |
| DDR2 | AK095975 | FLJ38656AAAN |
| LDLR | NM_000527.2 | FLJ50672AAAN |
| ADAM18 | NM_014237.2 | FLJ94607AAAN |
| PLAT | NM_33011.1 | FLJ93864AAAN |
| DARS | AK129521 | FLJ26010AAAN |
| PIP4K2B | BC027459.1 | FLJ07011AAAN |
| SFXN1 | AK056915 | FLJ32353AAAN |
| BCAP31 | AK057613 | FLJ33051AAAN |
| TNFSF15 | NM_005118.3 | FLJ75718AAAN |
| IFNB1 | NM_002176.2 | FLJ08204AAAN |
| MBP | AK128770 | FLJ45270AAAN |
| MAFK | AK092414 | FLJ35095AAAN |
| CD59 | NM_203331.2 | FLJ92039AAAN |
| INS | BC005255.1 | FLJ80205AAAN |
| HTN3 | AK130503 | FLJ26993AAAN |
| PBK | NM_018492.2 | FLJ14385AAAN |
| PSG1 | NM_001184825.1 | FLJ85824AAAN |
| CXorf61 | NM_001017978.2 | FLJ20611AAAN |
| SSX2B | NM_001164417.1 | FLJ81708SAAN |
| TULP2 | NM_003323.2 | FLJ81202AAAF |
| COX6B2 | NM_144613.4 | FLJ85805AAAN |

Almost entire amounts of 28 Types of the proteins having the insolubilizing tags attached thereto (Table 9), based on the amount contained in the insolubilized fraction, were re-solubilized by Solvent 23. Based on the results of this Test Example, the tagged proteins having the protein tag according to the present invention attached thereto were proven to be re-solubilizable by using a solvent containing SDS at a concentration of 0.04% (w/v) after being recovered into the insolubilized fraction.

INDUSTRIAL APPLICABILITY

A protein tag of the present invention allows a recombinant protein to be recovered at a high yield in a convenient manner, thereby enabling global protein purification. Accordingly, the protein tag according to the present invention can be utilized in basic and clinical researches using proteins, peptides, anti-protein antibodies, and the like in the medical, pharmaceutical, and biological fields.

The invention claimed is:

1. A protein tag set forth by SEQ ID NO: 2, 3, or 4.

2. A fusion protein comprising a target protein tagged with the protein tag of claim 1.

3. A protein array in which the fusion protein of claim 2 is immobilized on a support.

4. A vector expressing the protein tag of claim 1.

5. The vector of claim 4 which expresses the fusion protein of claim 2.

6. A protein purification method comprising:
   providing an expression vector encoding a fusion protein, wherein the fusion protein comprises a target protein fused to the protein tag of claim 1;
   expressing the fusion protein in a cell-free protein synthesis system or a cell-associated protein synthesis system; and
   a purification step for purifying the fusion protein.

7. The protein purification method of claim 6, wherein the cell-free protein synthesis system is a wheat germ cell-free protein synthesis system.

8. The protein purification method of claim 6 or 7, wherein the purification step comprises centrifuging the fusion protein.

9. A method for purifying an antibody to a target protein, the antibody purification method comprising binding the antibody to a fusion protein comprising the target protein tagged with the protein tag of claim 1.

10. The protein tag of claim 1, where in protein tag is set forth by SEQ ID NO: 2.

11. The protein tag of claim 1, where in protein tag is set forth by SEQ ID NO: 3.

12. The protein tag of claim 1, where in protein tag is set forth by SEQ ID NO: 4.

* * * * *